(12) United States Patent
Forsyth et al.

(10) Patent No.: US 12,667,408 B2
(45) Date of Patent: Jun. 30, 2026

(54) CONTROL SYSTEM AND USER INTERFACE FOR AN ABLATION SYSTEM

(71) Applicant: BOSTON SCIENTIFIC SCIMED, INC., Maple Grove, MN (US)

(72) Inventors: Bruce R. Forsyth, Hanover, MN (US); Jonathan Tyler Gorzycki, Blaine, MN (US); Larry D. Canady, Jr., Ham Lake, MN (US); Hong Cao, Maple Grove, MN (US); Timothy A. Ostroot, Cokato, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 213 days.

(21) Appl. No.: 18/440,282

(22) Filed: Feb. 13, 2024

(65) Prior Publication Data

US 2024/0216037 A1      Jul. 4, 2024

Related U.S. Application Data

(63) Continuation of application No. 17/070,649, filed on Oct. 14, 2020, now Pat. No. 11,931,094.

(Continued)

(51) Int. Cl.
*A61B 18/12*      (2006.01)
*A61B 18/14*      (2006.01)
*A61B 18/00*      (2006.01)

(52) U.S. Cl.
CPC ...... *A61B 18/1206* (2013.01); *A61B 18/1492* (2013.01); *A61B 2018/00351* (2013.01);

(Continued)

(58) Field of Classification Search
CPC ............ A61B 18/1206; A61B 18/1233; A61B 18/1492; A61B 2018/00351;

(Continued)

(56) References Cited

U.S. PATENT DOCUMENTS 5,019,034 A      5/1991   Weaver et al.
5,370,675 A      12/1994   Edwards et al.
(Continued)

FOREIGN PATENT DOCUMENTS

JP          H11346436 A      12/1999
WO          2008102154 A2      8/2008
(Continued)

OTHER PUBLICATIONS

StarBurst XL RFA Electrodes, Angiodynamics Inc. 2013. 2 pages.
(Continued)

*Primary Examiner* — Daniel W Fowler
(74) *Attorney, Agent, or Firm* — Seager, Tufte & Wickhem LLP

(57)      ABSTRACT

Electrosurgical generators having improved functionality and a user interface. In an example, the user may modify therapy output parameters without interrupting therapy delivery within a therapy regimen by accessing a change tool on the user interface, with the change tool operable to change a stack selector configuration. In an example, the display shows both therapy amplitudes and encountered impedances for a plurality of therapy pulses in different portions of a display.

13 Claims, 23 Drawing Sheets

Related U.S. Application Data

(60) Provisional application No. 62/915,489, filed on Oct. 15, 2019.

(52) U.S. Cl.
CPC .............. *A61B 2018/00577* (2013.01); *A61B 2018/00613* (2013.01); *A61B 2018/00702* (2013.01); *A61B 2018/00839* (2013.01); *A61B 2018/00875* (2013.01); *A61B 2018/00958* (2013.01); *A61B 2018/00982* (2013.01)

(58) Field of Classification Search
CPC   A61B 2018/00577; A61B 2018/00613; A61B 2018/00642; A61B 2018/00702; A61B 2018/00726; A61B 2018/00761; A61B 2018/00767; A61B 2018/00839; A61B 2018/00875; A61B 2018/00898; A61B 2018/00985; A61B 2018/00982; A61B 2018/124

See application file for complete search history.

(56) References Cited

U.S. PATENT DOCUMENTS

| | | | |
|---|---|---|---|
| 5,718,246 | A | 2/1998 | Vona |
| 5,855,576 | A | 1/1999 | Leveen et al. |
| 5,863,290 | A | 1/1999 | Gough et al. |
| 6,010,613 | A | 1/2000 | Walters et al. |
| 6,041,252 | A | 3/2000 | Walker et al. |
| 6,043,066 | A | 3/2000 | Mangano et al. |
| 6,278,895 | B1 | 8/2001 | Bernard |
| 6,326,177 | B1 | 12/2001 | Schoenbach et al. |
| 6,387,671 | B1 | 5/2002 | Rubinsky et al. |
| 6,428,534 | B1 | 8/2002 | Joye et al. |
| 6,638,277 | B2 | 10/2003 | Schaefer et al. |
| 6,714,816 | B1 | 3/2004 | Heller et al. |
| 6,912,471 | B2 | 6/2005 | Heigl et al. |
| 6,994,706 | B2 | 2/2006 | Chornenky et al. |
| 7,245,963 | B2 | 7/2007 | Draghia-Akli et al. |
| 7,306,595 | B2 | 12/2007 | Ostrovsky et al. |
| 7,306,940 | B2 | 12/2007 | Miklavcic et al. |
| 7,416,549 | B2 | 8/2008 | Young et al. |
| 7,456,012 | B2 | 11/2008 | Ryttsn et al. |
| 7,794,458 | B2 | 9/2010 | Mcintyre et al. |
| 7,799,022 | B2 | 9/2010 | Fernald et al. |
| 7,850,681 | B2 | 12/2010 | Lafontaine |
| 8,014,854 | B2 | 9/2011 | Schroeppel et al. |
| 8,048,067 | B2 | 11/2011 | Davalos et al. |
| 8,114,070 | B2 | 2/2012 | Rubinsky et al. |
| 8,152,801 | B2 | 4/2012 | Goldberg et al. |
| 8,211,104 | B2 | 7/2012 | Mccullagh et al. |
| 8,251,986 | B2 | 8/2012 | Chornenky et al. |
| 8,282,631 | B2 | 10/2012 | Davalos et al. |
| 8,465,484 | B2 | 6/2013 | Davalos et al. |
| 8,540,710 | B2 | 9/2013 | Johnson et al. |
| 8,603,087 | B2 | 12/2013 | Rubinsky et al. |
| 8,647,338 | B2 | 2/2014 | Chornenky et al. |
| 8,801,709 | B2 | 8/2014 | Prakash et al. |
| 8,915,911 | B2 | 12/2014 | Azure |
| 8,920,416 | B2 | 12/2014 | Pham et al. |
| 8,926,606 | B2 | 1/2015 | Davalos et al. |
| 9,005,189 | B2 | 4/2015 | Davalos et al. |
| 9,168,096 | B2 | 10/2015 | Kreindel |
| 10,105,172 | B2 | 10/2018 | Johnson et al. |
| 10,154,869 | B2 | 12/2018 | Onik et al. |
| 11,045,648 | B2 | 6/2021 | Dewitt et al. |
| 2001/0044596 | A1 | 11/2001 | Jaafar |
| 2002/0107515 | A1 | 8/2002 | Edwards et al. |
| 2002/0115991 | A1 | 8/2002 | Edwards |
| 2003/0009110 | A1 | 1/2003 | Tu et al. |
| 2004/0015163 | A1 | 1/2004 | Buysse et al. |
| 2004/0186468 | A1 | 9/2004 | Edwards |
| 2005/0267467 | A1 | 12/2005 | Paul et al. |
| 2006/0142801 | A1 | 6/2006 | Demarais et al. |
| 2006/0293730 | A1 | 12/2006 | Rubinsky et al. |
| 2007/0025919 | A1 | 2/2007 | Deem et al. |
| 2007/0282314 | A1* | 12/2007 | Berry .................. A61B 18/203 |
| | | | 606/9 |
| 2008/0275445 | A1 | 11/2008 | Kelly et al. |
| 2009/0247933 | A1 | 10/2009 | Maor et al. |
| 2009/0254148 | A1 | 10/2009 | Borgens et al. |
| 2009/0326638 | A1 | 12/2009 | Atanasoka et al. |
| 2010/0023004 | A1 | 1/2010 | Francischelli et al. |
| 2010/0250209 | A1 | 9/2010 | Pearson et al. |
| 2010/0261994 | A1 | 10/2010 | Davalos et al. |
| 2011/0106221 | A1 | 5/2011 | Neal, II et al. |
| 2011/0170321 | A1 | 7/2011 | Schall et al. |
| 2011/0238057 | A1 | 9/2011 | Moss et al. |
| 2012/0053403 | A1 | 3/2012 | Ducharme et al. |
| 2012/0197356 | A1 | 8/2012 | Wei et al. |
| 2012/0220999 | A1 | 8/2012 | Long |
| 2012/0310230 | A1 | 12/2012 | Willis |
| 2012/0330299 | A1 | 12/2012 | Webster et al. |
| 2013/0030430 | A1 | 1/2013 | Stewart et al. |
| 2013/0184702 | A1 | 7/2013 | Neal, II et al. |
| 2014/0121663 | A1 | 5/2014 | Pearson et al. |
| 2014/0128859 | A1 | 5/2014 | Lee |
| 2014/0128936 | A1 | 5/2014 | Laufer et al. |
| 2016/0058493 | A1 | 3/2016 | Neal, II et al. |
| 2016/0113709 | A1 | 4/2016 | Maor |
| 2016/0199661 | A1 | 7/2016 | Willard et al. |
| 2017/0035499 | A1 | 2/2017 | Stewart |
| 2017/0065313 | A1 | 3/2017 | Mickelsen |
| 2017/0105793 | A1 | 4/2017 | Cao et al. |
| 2017/0140121 | A1 | 5/2017 | Schulhauser et al. |
| 2017/0245928 | A1* | 8/2017 | Xiao .................... H03K 17/687 |
| 2017/0325872 | A1 | 11/2017 | Friedrichs et al. |
| 2017/0348525 | A1* | 12/2017 | Sano ................. A61B 18/1206 |
| 2018/0235576 | A1 | 8/2018 | Brannan |
| 2018/0250508 | A1 | 9/2018 | Howard |
| 2018/0272124 | A1 | 9/2018 | Kibler et al. |
| 2018/0303543 | A1 | 10/2018 | Stewart et al. |
| 2019/0030328 | A1 | 1/2019 | Stewart et al. |
| 2019/0083169 | A1 | 3/2019 | Single et al. |
| 2019/0143106 | A1 | 5/2019 | Dewitt et al. |
| 2019/0223938 | A1 | 7/2019 | Arena et al. |
| 2019/0223943 | A1 | 7/2019 | Forsyth et al. |
| 2019/0336198 | A1 | 11/2019 | Viswanathan et al. |
| 2020/0129230 | A1 | 4/2020 | Forsyth et al. |
| 2020/0155227 | A1 | 5/2020 | Cao et al. |
| 2020/0289185 | A1 | 9/2020 | Forsyth et al. |
| 2020/0289188 | A1 | 9/2020 | Forsyth et al. |
| 2020/0289827 | A1 | 9/2020 | Forsyth et al. |

FOREIGN PATENT DOCUMENTS

| | | |
|---|---|---|
| WO | 2015021113 A1 | 2/2015 |
| WO | 2017119934 A1 | 7/2017 |
| WO | 2018200800 A1 | 11/2018 |

OTHER PUBLICATIONS

StarBurst Talon Fusion RFA Electrodes, Angiodynamics Inc. 2013. 2 pages.

Deodhar et al; "Irreversible Electroporation Near the Heart: Ventricular Arrhythmias Can Be Prevented With ECG Synchronization." AJR 196:W330-W335, Mar. 2011. Accessed on Jul. 16, 2019.

Beebe et al; "Nanosecond Pulsed Electric Field (nsPEF) Effects on Cells and Tissues: Apoptosis Induction and Tumor Growth Inhibition", IEEE Transactions on Plasma Science , 6 pages, Mar. 2002.

Kennedy et al; "Cationic Peptide Exposure Enhances Pulsed-Electric-Field-Mediated Membrane Disruption", PLOS ONE, vol. 9, Issue 3, 17 pp. Mar. 2014.

Miklavcic et al; "The Importance of Electric Field Distribution for Effective in Vivo Electroporation of Tissues", Biophysical Journal, vol. 74, pp. 2152-2158, May 1998.

Distelmaier et al; "Midterm Safety and Efficacy of Irreversible Electroporation of Malignant Tumors Located Close to Major Portal or Hepatic Veins", Radiology, vol. 285, No. 3, 1023-1031, Dec. 2017.

(56) References Cited

OTHER PUBLICATIONS

Rubinsky et al; "Irreversible Electroporation: A New Ablation Modality—Clinical Implications." Technology in Cancer Research and Treatment, vol. 6, No. 1, pp. 37-48, Feb. 2007.

Swartz et al; "Sparking New Frontiers: Using in Vivo Electroporation for Genetic Manipulations", Developmental Biology, 233, pp. 13-21, 2001.

Tsong, "Electroporation of Cell Membranes," Biophysical Journal, vol. 60, pp. 297-306, Aug. 2, 1991.

International Search Report and Written Opinion dated Jul. 2, 2020 for International Application No. PCT/US2020/022582.

International Search Report and Written Opinion Dated Jul. 7, 2020 for International Application No. PCT/US2020/022571.

International Search Report and Written Opinion dated Jun. 26, 2020 for International Application No. PCT/US2020/022578.

Invitation to Pay Additional Fees dated Jan. 28, 2021 for International Application No. PCT/US2020/055577.

* cited by examiner

350

1
(+) Enabled

2
(-) Enabled

3
(-) Enabled

4
(+) Enabled

| Phase # | Anode(s) | Cathode(s) | Indifferent | Pulsewidth (us) | Amplitude (V) | Off After (us) |
|---------|----------|------------|-------------|-----------------|---------------|----------------|
| 1 | A | B | C | 40 | 1000 | 10 |
| Add another? | | | | | | |
| Finish? | | | | | | |

FIG. 14A

| Phase # | Anode(s) | Cathode(s) | Indifferent | Pulsewidth (us) | Amplitude (V) | Off After (us) |
|---------|----------|------------|-------------|-----------------|---------------|----------------|
| 1 | A | B | C | 40 | 1000 | 10 |
| 2 | B | C | A | 40 | 1000 | 10 |
| Add another? | | | | | | |
| Finish? | | | | | | |

FIG. 14B

| Phase | Anode | Cath. | Neut. | PW (us) | Volts | Post (us) |
|-------|-------|-------|-------|---------|-------|-----------|
| 1 | A | B | C | 40 | 1000 | 10 |
| 2 | B | C | A | 40 | 1000 | 10 |

Add another?

Finish?

Probe Type:

FIG. 15

CONTROL SYSTEM AND USER INTERFACE FOR AN ABLATION SYSTEM

CROSS REFERENCE TO RELATED APPLICATIONS

The present application is a continuation of U.S. patent application Ser. No. 17/070,649, filed Oct. 14, 2020, titled CONTROL SYSTEM AND USER INTERFACE FOR AN ABLATION SYSTEM, which claims the benefit of and priority to U.S. Provisional App. No. 62/915,489, titled CONTROL SYSTEM AND USER INTERFACE FOR AN ABLATION SYSTEM, filed Oct. 15, 2019, the disclosures of which are incorporated herein by reference.

BACKGROUND

Removal or destruction of diseased tissue is a goal of many cancer treatment methods. Tumors may be surgically removed, however, less invasive approaches garner much attention. Tissue ablation is a minimally invasive method of destroying undesirable tissue in the body. A variety of ablation techniques have been developed, many using the application of electricity or other energy via a probe placed on or inserted into or adjacent target tissue. For example, heat-based thermal ablation adds heat to destroy tissue. Radio-frequency (RF) thermal, microwave and high intensity focused ultrasound ablation can each be used to raise localized tissue temperatures well above the body's normal 37 degrees C. Irreversible electroporation (IRE) uses electric fields to expand pores in the cell membrane beyond the point of recovery, causing cell death for want of a patent cell membrane. The spatial characteristics of the applied field control which cells and tissue will be affected, allowing for better selectivity in the treatment zone than with thermal techniques. IRE typically uses a narrower pulse width than RF ablation to reduce thermal effects.

User interfaces and control systems for ablation procedures have historically been either highly technical, requiring a very skilled operator to use, or rudimentary. As multiple different approaches to ablation are developed, new and alternative control systems and user interfaces are desired.

OVERVIEW

The present inventors have recognized, among other things, that a problem to be solved is the need for new and/or alternative user interfaces and control systems that provide control over the parameters needed by the user to define different ablation techniques without unnecessarily complicating procedure setup and control.

An illustrative, non-limiting apparatus example takes the form of an electrosurgical generator comprising: one or more ports adapted to receive one or more electrosurgical probes, each port comprising at least one contact; a high voltage power source; delivery circuitry comprising a plurality of switches configured to route an output from the power source to selected contacts of the one or more ports; a controller having stored instructions that can be selected, configured or adjusted by a user, the stored instructions including at least one instruction set for delivering a therapy regimen, the therapy regimen comprising a plurality of pulses each having a pulse amplitude and a pulse width, the instruction set defining the pulse amplitude and the pulse width and optionally pulse repetition rate; and a user interface having a user operable change tool that the user can actuate to modify the pulse amplitude without stopping or interrupting the therapy regimen.

Additionally or alternatively, the high voltage power source comprises at least first and second capacitors configured for outputting therapy pulses, and a stack selector comprising a plurality of switches responsive to the change tool to include, in a first configuration, all of the capacitors for purposes of outputting therapy pulses, and in a second configuration, less than all of the capacitors for purposes of outputting therapy pulses.

Additionally or alternatively, the high voltage power source is coupled to a voltage step down circuit responsive to the change tool to route a higher or lower voltage from the high voltage power source to the delivery circuitry.

Additionally or alternatively, the instruction set for delivering the therapy regimen comprises a series of pulses grouped as a burst, the therapy regimen defining how many pulses are in a burst and, optionally, a burst repetition rate, wherein the controller further comprises an executable triggering instruction set adapted to receive or identify a therapy trigger, identify a therapy window for delivery of a therapy burst from within the therapy regimen relative to the therapy trigger, and instruct the delivery circuit to route a therapy burst to selected contacts of the one or more ports.

Additionally or alternatively, the instruction set for delivering the therapy regimen comprises a series of pulses grouped as a burst, the therapy regimen defining how many pulses are in a burst, further comprising a trigger circuit adapted to sense or receive a representation of a cardiac signal of a patient, identify a therapy window for delivery of a therapy burst from within the therapy regimen, and instruct the delivery circuit to route a therapy burst to selected contacts of the one or more ports.

Another illustrative, non-limiting apparatus example takes the form of an electrosurgical generator comprising: one or more ports adapted to receive one or more electrosurgical probes, each port comprising at least one contact; a high voltage power source; delivery circuitry comprising a plurality of switches configured to route an output from the power source to selected contacts of the one or more ports; a controller having stored instructions that can be selected, configured or adjusted by a user, the stored instructions including at least one instruction set for delivering a therapy regimen, the therapy regimen defining a multi-polar output sequence in which at least three electrodes are used, with a first selection of the electrodes used to deliver a first pulse and a second selection of the electrodes, different from the first selection of the electrodes, used to deliver a second pulse; a measurement circuitry configured to measure impedance during delivery of a therapy pulse including one or more of a current sensor or a voltage sensor; a user interface configured for displaying therapy delivery parameters during or after generation of the therapy regimen, the user interface displaying in the amplitude of the first pulse and the second pulse in a first portion of the user interface and impedance encountered by the first and second pulses in a second portion of the user interface, to facilitate comparison of the first and second pulse amplitudes and impedances.

Additionally or alternatively, the controller further comprises an executable triggering instruction set adapted to sense or receive a representation of a cardiac signal of a patient, identify a therapy window for delivery of a therapy burst from within the therapy regimen, and instruct the delivery circuit to route a therapy burst to selected contacts of the one or more ports.

Additionally or alternatively, the electrosurgical generator further includes a trigger circuit adapted to sense or receive a representation of a cardiac signal of a patient, identify a therapy window for delivery of a therapy burst from within the therapy regimen, and instruct the delivery circuit to route a therapy burst to selected contacts of the one or more ports.

Another illustrative, non-limiting apparatus example takes the form of an electrosurgical generator comprising: one or more ports adapted to receive one or more electrosurgical probes, each port comprising at least one contact; a high voltage power source; delivery circuitry comprising a plurality of switches configured to route an output from the power source to selected contacts of the one or more ports; a controller having stored instructions that can be selected, configured or adjusted by a user, the stored instructions including at least one instruction set for delivering a therapy regimen, the therapy regimen comprising a series of pulses each having a pulse width, the series of pulses forming a burst, the instruction set defining how many pulses are in each burst and defining how many bursts are to be delivered in the therapy regimen and, optionally, one or more of a pulse repetition rate and/or a burst repetition rate; a trigger adapted to sense or receive a triggering signal from a patient, the trigger configured to identify a therapy window for delivery of a burst defined by the therapy regimen and command the delivery circuitry to route the output to selected contacts during the therapy window, wherein the controller further includes a stored timer instruction set adapted to determine time remaining for the therapy regimen by determining a trigger rate using data from the trigger, and calculate how much time will be required to complete remaining bursts of the therapy regimen in light of the trigger rate; and a user interface having a display section that displays to a user an estimated remaining time as calculated by the controller executing the stored timer instruction set.

Additionally or alternatively, the trigger is a dedicated circuit and a lead system having electrocardiogram (ECG) electrodes thereon for capturing a cutaneous cardiac signal from a patient, the dedicated circuit including a cardiac signal detector for detecting components of the cardiac signal and thereby detecting cardiac cycles.

Additionally or alternatively, the trigger is a stored trigger instruction set operable by the controller, the electrosurgical generator comprising a wireless transceiver comprising an antenna, amplifier, and demodulator to facilitate receipt of a wireless signal from an ECG detector issuing cardiac signal related data including indications of when a selected component of the cardiac signal occurs, wherein the controller is configured to receive cardiac signal related data from the wireless transceiver while executing the stored trigger instruction set.

Additionally or alternatively, the trigger is configured to wait for expiration of user configurable delay period after a triggering signal is observed or received before the therapy window, and the user interface allows the user to select the configurable delay period.

Additionally or alternatively, the user interface comprises an amplitude display allowing the user to set or adjust therapy amplitude and, in conjunction with the amplitude display, the user interface is also adapted to display an estimate of the amplitude that will be delivered to tissue between a selected pair of electrodes on a probe coupled to the one or more ports.

Additionally or alternatively, the user interface comprises a waveform selector allowing a user to select from at least biphasic and monophasic waveform types.

Additionally or alternatively, the user interface comprises a waveform design tool allowing a user to select an interval between pulses in each burst, a quantity of pulses to provide in each burst, and a quantity of bursts to deliver, and the controller is responsive to the waveform design tool to select, configure, or adjust an instruction set defining the therapy regimen.

Additionally or alternatively, the controller is configured to store first and second therapy logs for delivery of the therapy regimen as follows: the first log comprising input and output parameters of therapy as delivered; and the second log recording raw waveforms as delivered to the patient.

Additionally or alternatively, the user interface comprises a pause button or icon operable to interrupt a therapy regimen without terminating the therapy regimen.

Some illustrative, non-limiting system examples take the form of a system for treating a patient by ablation of a target tissue comprising an electrosurgical generator as any of the preceding illustrative, non-limiting apparatus examples, and a probe configured for use with the electrosurgical generator.

An illustrative, non-limiting method example takes the form of a method of treating a patient by ablation of a target tissue using an electrosurgical generator having a user interface, the method comprising: initiating a therapy regimen comprising a series of pulses each having a pulse amplitude and a pulse width; and actuating a user operable change tool accessible via the user interface to modify the pulse amplitude without stopping or interrupting the therapy regimen. The therapy regimen may further define one or more of a pulse repetition rate and/or a burst repetition rate.

Additionally or alternatively, the electrosurgical generator comprises a high voltage power source having at least first and second capacitors configured for outputting therapy pulses, and a stack selector comprising a plurality of switches responsive to the change tool to include, in a first configuration, all of the capacitors for outputting therapy pulses, and in a second configuration, less than all of the capacitors for outputting therapy pulses, wherein the step of actuating the user operable change tool causes switching of the electrosurgical generator between the first and second configurations.

Additionally or alternatively, wherein the electrosurgical generator comprises a high voltage power source and a voltage step down circuit responsive to the user operable change tool to route a higher or lower voltage from the high voltage power source to the delivery circuitry.

Additionally or alternatively, the therapy regimen is a triggered therapy regimen making use of a triggering circuit in the electrosurgical generator or a stored instruction set operable by the electrosurgical generator for providing triggered therapy using a biological signal.

Another illustrative, non-limiting method example takes the form of a method of delivering ablation therapy to a patient in an electrosurgical generator having one or more ports adapted to receive one or more electrosurgical probes, each port comprising at least one contact; a high voltage power source; delivery circuitry comprising a plurality of switches configured to route an output from the power source to selected contacts of the one or more ports; a controller having stored instructions that can be selected, configured or adjusted by a user, the stored instructions including at least one instruction set for delivering a therapy regimen, the therapy regimen defining a multi-polar output sequence in which at least three electrodes are used, with a first selection of the electrodes used to deliver a first pulse and a second selection of the electrodes, different from the first selection of the electrodes, used to deliver a second pulse; a measurement circuitry configured to measure impedance during delivery of a therapy pulse including one or more of a current sensor or a voltage sensor; a user interface configured for displaying therapy delivery parameters during or after generation of the therapy regimen, the method comprising: delivering at least the first and second pulses; measuring impedance encountered by each of the first and second pulses; displaying in the amplitude of the first pulse and the second pulse in a first portion of the user interface; and displaying impedance encountered by the first and second pulses in a second portion of the user interface, thereby facilitating comparison of the first and second pulse amplitudes and impedances.

Additionally or alternatively, wherein the therapy regimen is a triggered therapy regimen making use of a triggering circuit in the electrosurgical generator or a stored instruction set operable by the electrosurgical generator for providing triggered therapy using a biological signal.

Another illustrative, non-limiting method example takes the form of a method of operation in an electrosurgical generator having one or more ports adapted to receive one or more electrosurgical probes, each port comprising at least one contact; a high voltage power source; delivery circuitry comprising a plurality of switches configured to route an output from the power source to selected contacts of the one or more ports; a controller having stored instructions that can be selected, configured or adjusted by a user, the stored instructions including at least one instruction set for delivering a therapy regimen, the therapy regimen comprising a series of pulses each having a pulse width, the series of pulses forming a burst, the instruction set defining how many pulses are in each burst and defining how many bursts are to be delivered in the therapy regimen; a trigger adapted to sense or receive a triggering signal from a patient, the trigger configured to identify a therapy window for delivery of a burst defined by the therapy regimen; the method comprising: delivering at least two therapy bursts in response to at least two triggering signals; determining a trigger rate using data from the trigger; calculating how much time will be required to complete remaining bursts of the therapy regimen in light of the trigger rate; and displaying via the a user interface an estimated remaining time as calculated by the stored timer instruction set.

Additionally or alternatively, the trigger relies on cutaneous cardiac signal from a patient, such that the estimated remaining time relates to cardiac cycle rate of the patient.

Additionally or alternatively, the method further comprises displaying each of a programmed amplitude and a delivered amplitude for therapy pulses.

Additionally or alternatively, the user interface comprises a waveform selector allowing a user to select from at least biphasic and monophasic waveform types.

An illustrative non-limiting user interface example takes the form of a user interface for an electrosurgical generator having a power supply, output circuitry, one or more ports for receiving an electrosurgical probe or probes, and control circuitry adapted to execute stored instructions to deliver bursts of therapy pulses, the user interface comprising a user selectable waveform type tool including each of the following: monophasic waveform type; biphasic waveform type, in which each therapy pulse comprises first and second phases each using the same electrodes but in opposite polarity; and three electrode rotating type, in which each therapy pulse comprises first, second and third phases using each of first, second and third electrode combinations; wherein the user interface presents options for each of the three waveform types, depending on which waveform type is selected, to the user to define the following: for a monophasic waveform type, amplitude, pulse width, and electrode selection for each monophasic pulse, a quantity of monophasic pulses and interpulse intervals to use in a burst, and a number of bursts to be delivered; for a biphasic waveform type, amplitude, pulse width, interphase delay and electrode selection for each biphasic pulse, a quantity of biphasic pulses and interpulse intervals to use in a burst, and a number of bursts to be delivered; and for a three electrode rotating type, selection of first, second and third electrode combinations for the first, second and third phases, amplitude, pulse width and interphase periods, a quantity of therapy pulses and interpulse intervals to use in each burst.

Another illustrative, non-limiting method example takes the form of a method of displaying a therapy status in an ablation system while delivering therapy, the method comprising: initially determining a quantity of pulse bursts to be delivered, in which each pulse burst comprising a plurality of individual pulses; sensing a cardiac signal; initiating delivery of the quantity of pulse bursts, each pulse burst being delivered in a window between sensed cardiac events; displaying to a user each of a quantity of pulse bursts remaining and an estimated time remaining in the therapy, wherein the estimated time remaining is calculated by determining a cardiac rate and multiplying the cardiac rate by the number of pulse bursts remaining.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 11A-11B highlight features of a user interface with reference to FIG. 8;

FIG. 13 shows illustrative therapy electrodes;

FIGS. 14A-14C show additional illustrative therapy program interfaces; and

FIG. 15 shows an illustrative method of therapy delivery and status reporting.

DETAILED DESCRIPTION

Figure 1:
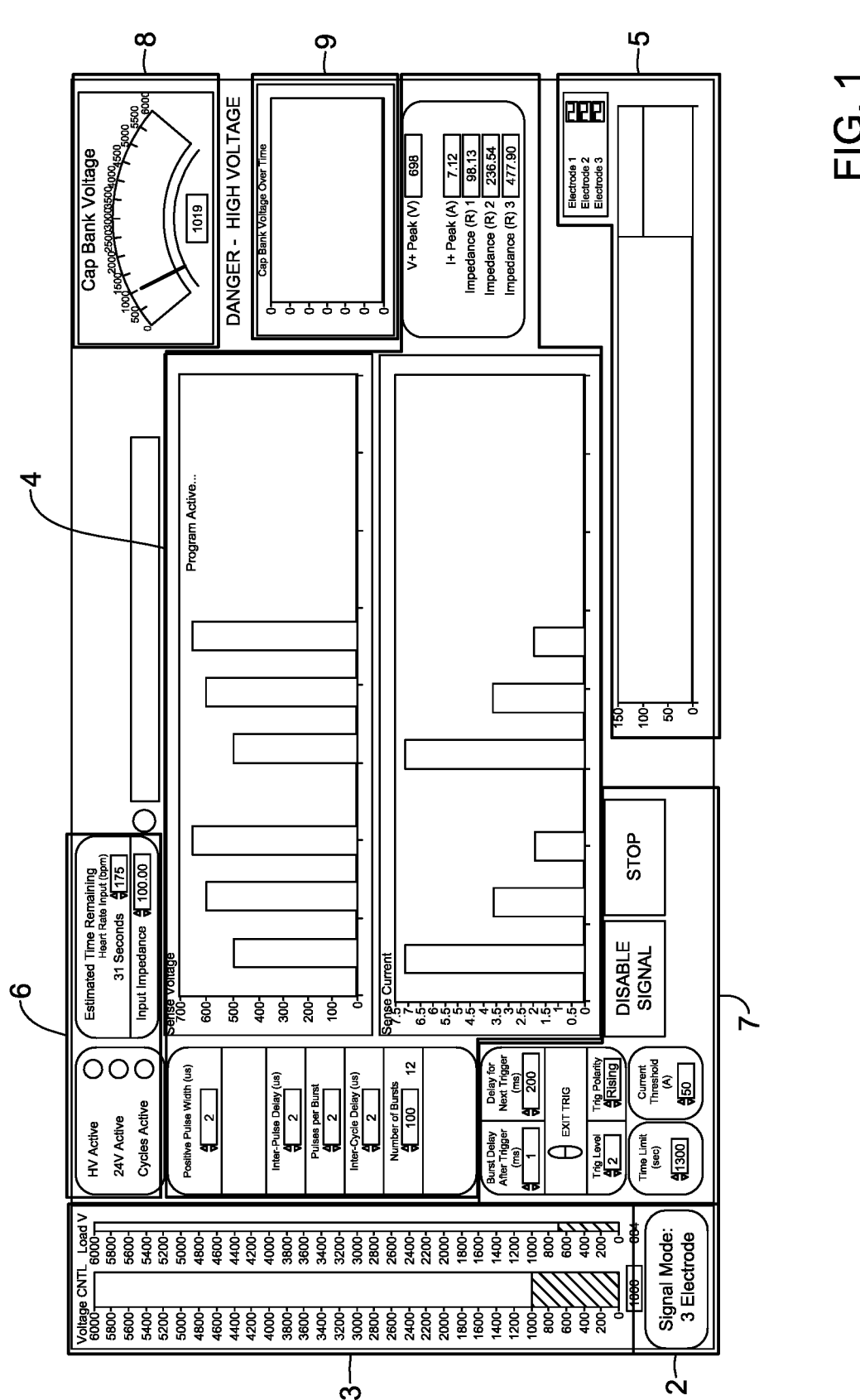
FIG. 1 illustrates a user interface for an electrosurgical apparatus.

FIG. 1 illustrates a user interface for an electrosurgical apparatus. Several sections of the user interface are shown with a border and will be discussed in greater detail below. Area 2 shows the output signal mode and is further described with reference to FIG. 2. Area 3 illustrates a voltage control in two parts: the generated (internal) signal and the in-tissue signal amplitudes, and is further described with reference to FIG. 3. Area 4 illustrates reporting of programmed voltage output and sensed current flow, along with programmed parameters for pulse width, delay and other features, and is further described with reference to FIGS. 4A-4C. Area 5 shows graphical illustration of impedances and is further described with reference to FIGS. 5A-5B. Area 6 shows active/inactive status and reports on the time remaining for a therapy regimen and is further described with reference to FIG. 6.

Area 8 illustrates the stored capacitor bank voltage in graphic form as well as with an exact number. As discussed below relative to FIG. 12, the electrosurgical apparatus may be designed with a capacitor bank that is charged to a relatively high voltage, in the hundreds or thousands of volts. The text immediately below area 8 provides a warning indicator that high voltage is present in the capacitor bank when a threshold "high voltage" is exceeded, such as 60 volts. In the example shown, a top stored voltage is in the range of about 6000 volts; higher or lower maximum values may be used, such as in the range of 1000 to 20,000 volts, or more or less. Area 9 provides a historical record of the capacitor bank voltage and is optional.

In the example of FIG. 1, the graphical user interface may be provided on a touchscreen and/or may be on a monitor used in association with user input devices well known in the art, such as a keyboard and mouse or trackball.

The electrosurgical apparatus may also be referred to as a signal generator. In a typical use configuration, one or more probes are plugged into the electrosurgical apparatus, with the probes then inserted into the patient or placed on the patient at a location in contact with, within, or adjacent to tissue to be treated such as an identified tumor, malignancy, or biological structure to be ablated. A return electrode may be placed on the patient elsewhere, such as with a cutaneous pad electrode, with the return electrode also coupled by wire to the electrosurgical generator. The probe or probes may have one or more electrodes thereon for outputting an electrical signal at a target position relative to the tissue to be ablated.

Figure 2:
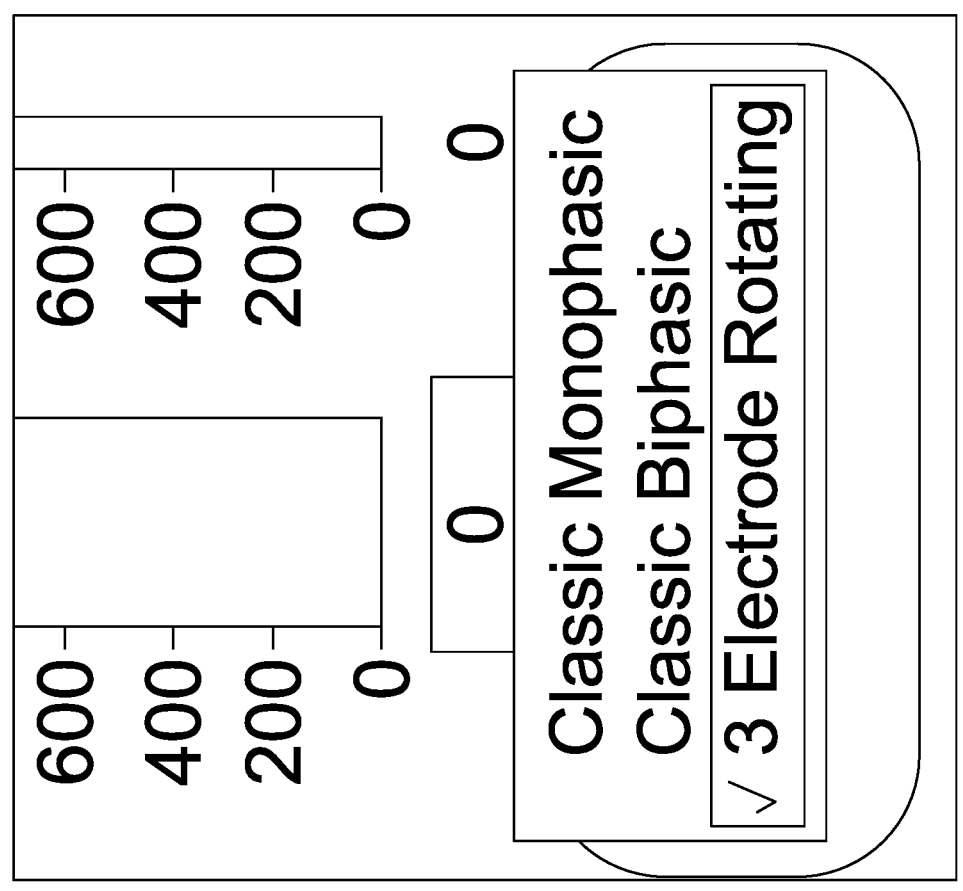
FIGS. 2, 3, 4A-4D, 5A-5B, 6 and 7 show details of illustrative user interfaces with reference to FIG. 1.

FIG. 2 illustrates the output signal mode selection of the system, highlighted as area 2 in FIG. 1. In this example, selecting the signal mode icon, such as by moving a mouse pointer and clicking or by touching a touchscreen brings up a dropdown list of signal modes that can be used. In this example, three modes are shown, including monophasic, biphasic and "3 electrode rotating" configurations.

A monophasic signal mode is one in which therapy electrodes on a probe used with the electrosurgical apparatus are used to deliver an output of a polarity, using one or more therapy electrodes on the probe as anode, and one or more other therapy electrodes on the prove as cathode. A separate return electrode pad may be used along with or in place of a therapy electrode on the probe for either anode or cathode, as desired. The output can have a pulse width and amplitude, but is not associated with a polarity reversal as would be the case with a biphasic signal mode.

As suggested in the preceding paragraph, a biphasic signal mode is one in which the output is delivered to a defined anode/cathode combination and, following delivery of a first pulse, an opposite polarity pulse is delivered. The anode electrodes become cathodes, and the cathode electrodes become anodes, in the second phase of a biphasic output.

Figure 13:
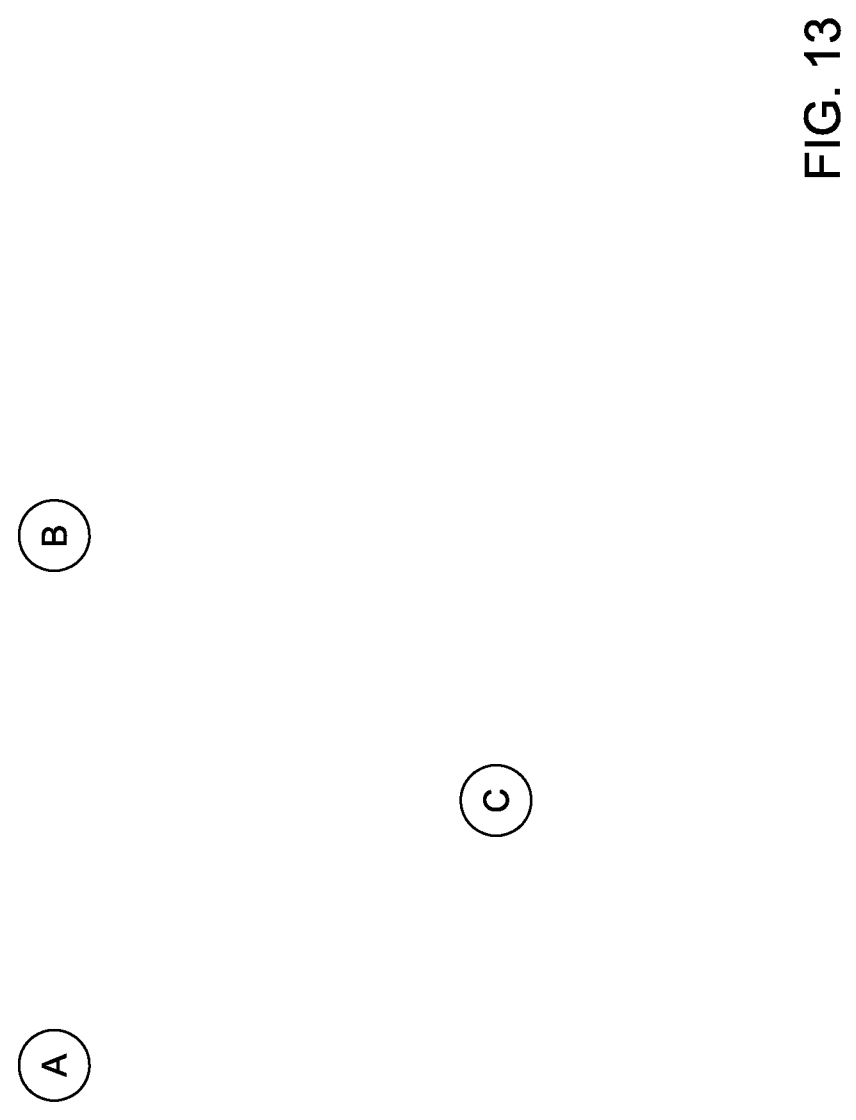

The three-electrode rotating configuration is one in which a sequence of three pulses are delivered as a combination using different selections of probe therapy electrodes and the return electrode pad for each phase. For example, with reference to FIG. 13, three electrodes A, B, C are shown. Following are some of the three-electrode rotating sequences that can be used:

| Anode | Cathode | Indifferent |
|-------|---------|-------------|
| A | B | C |
| B | C | A |
| C | A | B |

In this example, any of A, B or C may be a probe electrode or a return electrode. In another example:

| Anodes | Cathode | Indifferent |
|--------|---------|-------------|
| A, B | C | Return |
| A, C | B | Return |
| B, C | A | Return |

Here, each of A, B and C may be probe electrodes, while the indifferent electrode is a return electrode placed elsewhere on the patient. Providing an automated mode for a three electrode rotating configuration makes programming the system to provide a spatially and/or time multiplexed output easier than is possible with prior systems. The three electrode rotating approach is optional and may be omitted.

In another example, rather than a drop down menu, the user may be brought to a separate screen to define simple or complex waveforms having any number of phases with selectable electrodes for each phase. The programming sequence may be as shown in FIG. 14A. The user fills in the data as shown in the row for phase 1, and then clicks or taps on the icon for "Add Another" to create another phase, as shown by FIG. 14B. For each pulse within the waveform, the user can define, for example and without limitation, pulse width, pulse amplitude, and a duration of "off" time that follows the pulse before the start of a subsequent pulse. The "off" time may be omitted for the final pulse in the sequence, or may be treated as an inter-waveform off period. If the user has completed the waveform definition, the user can select the "Finish" icon. Additional columns may be provided to allow a user to define additional features, such as pulse shape (decaying, ramped, etc.). The interface may apply limits to the entries provided with reference to safety, usability, feasibility or other boundary conditions such as by limiting the maximum amplitude, minimum or maximum pulse width, maximum electrode usage. Such limits may apply to individual pulses as well as to an overall waveform, such as by limiting the amount of current imbalance through any given electrode or limiting duty cycle of a given electrode. In the example shown, Amplitude is indicated in terms of volts; a current-based Amplitude may be used instead, or a mix of amplitude and current defined pulses may be used.

Figure 14C:
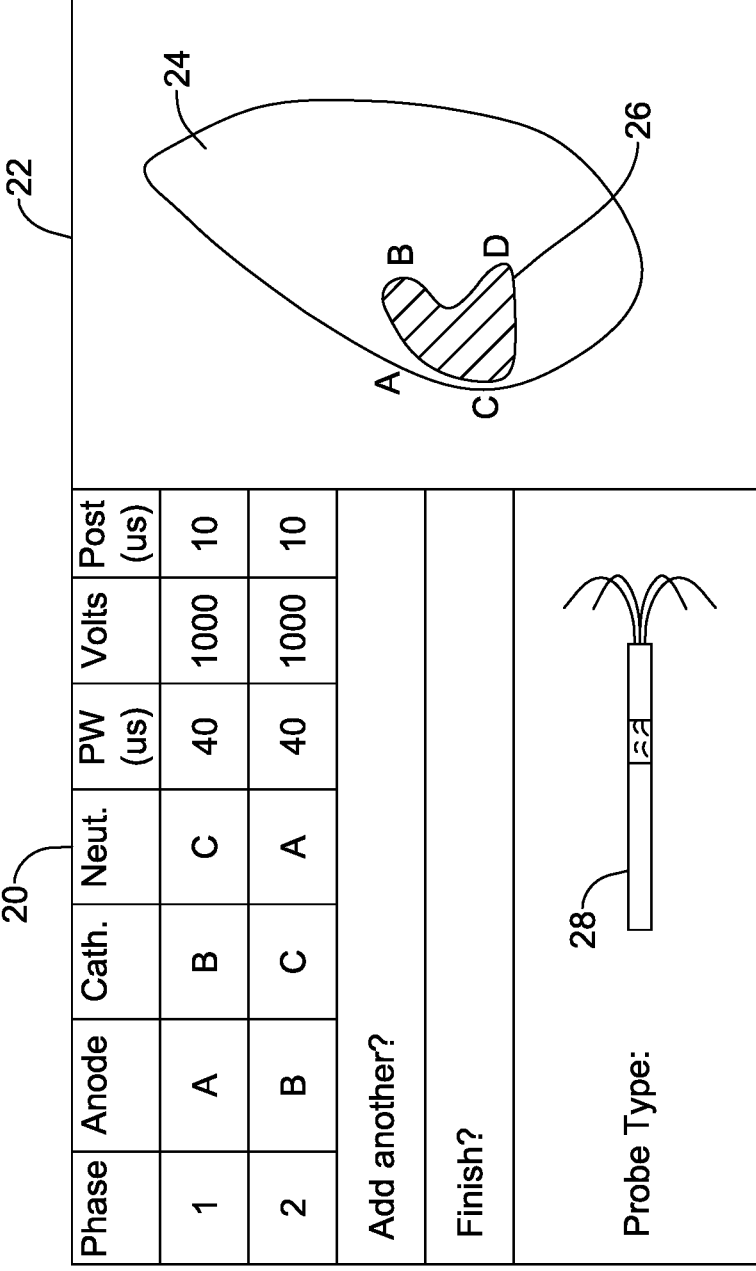
Figure 14C:

FIG. 14C shows another example. Here, the chart 20 is provided next to an image 22 that may aid in planning a therapy configuration. The image 22 includes a visual representation of a body organ 24 with a target tissue region 26 highlighted. Region 26 may be, for example, a tumor, and the image 22 may be imported electrically from a visualization system such as an ultrasound scanner that may be used preoperatively or as part of an operation itself to assess the target 26, for example by using a thumb drive or by wireless communication such as WIFI or Bluetooth. The letters A, B, C and D may illustrate target positions for the therapy electrodes. An image of the probe 28 may be provided as well for reference purposes.

Figure 3:
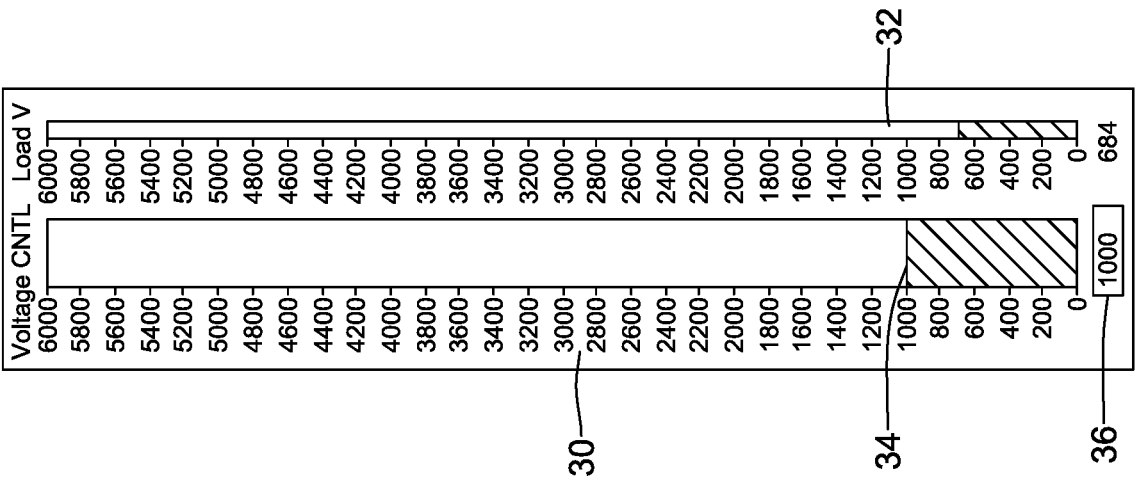

FIG. 3 illustrates a voltage control, and is highlighted as area 3 in FIG. 1. In this example, the voltage control is shown in two parts having the generated (internal) signal at 30, and the in-tissue signal amplitude that is applied as the therapy output at 32. The voltage is shown as a slider 34 on a scale of up to 6000 volts, though the available range of voltages is merely illustrative of one example. Other scales and top voltages may be used. In other examples a current maximum is shown rather than a voltage maximum, in which case the separate scale of the current as delivered would likely be omitted. In this example, the user can use a touchscreen, mouse, or other interface to move the slider 34 up and down to modify the available voltage. If the user would rather enter the voltage as text, a text box is provided at 36.

Figure 4A:
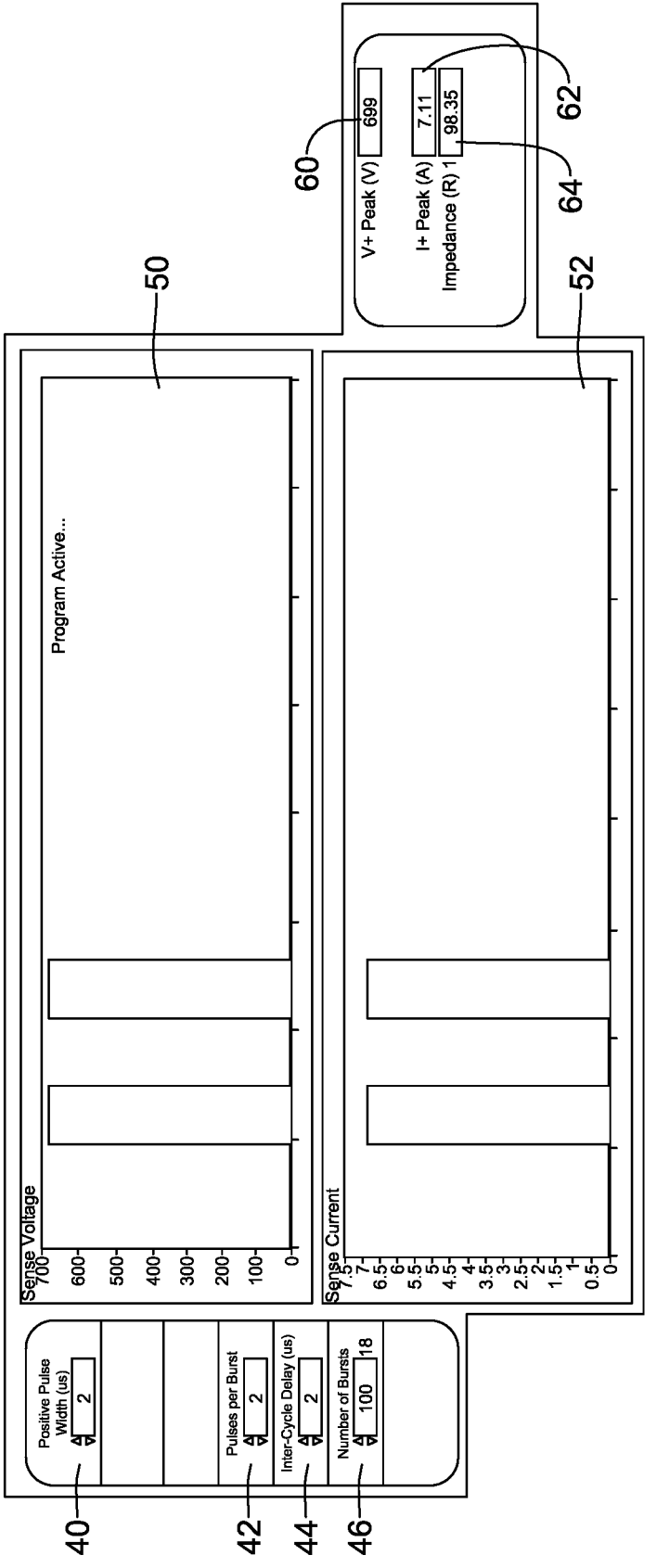
Figure 4B:
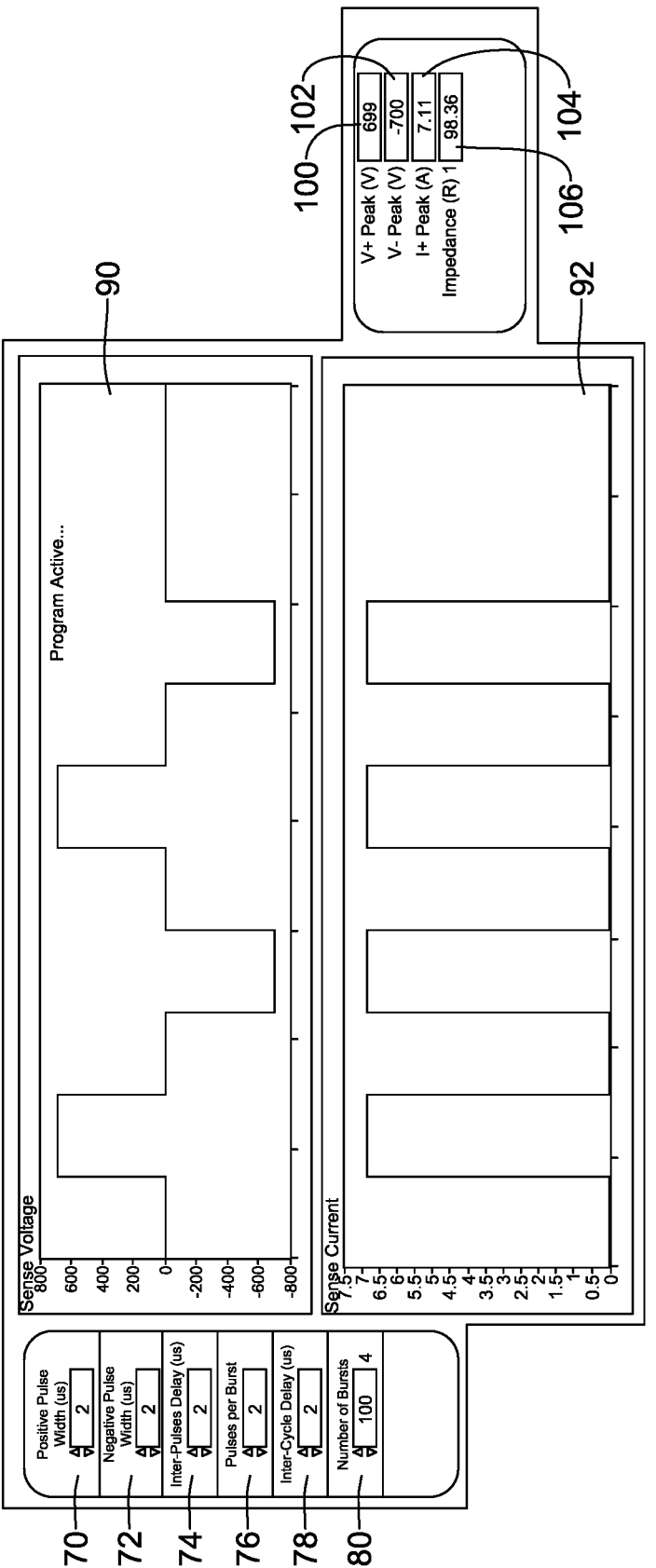
Figure 4C:
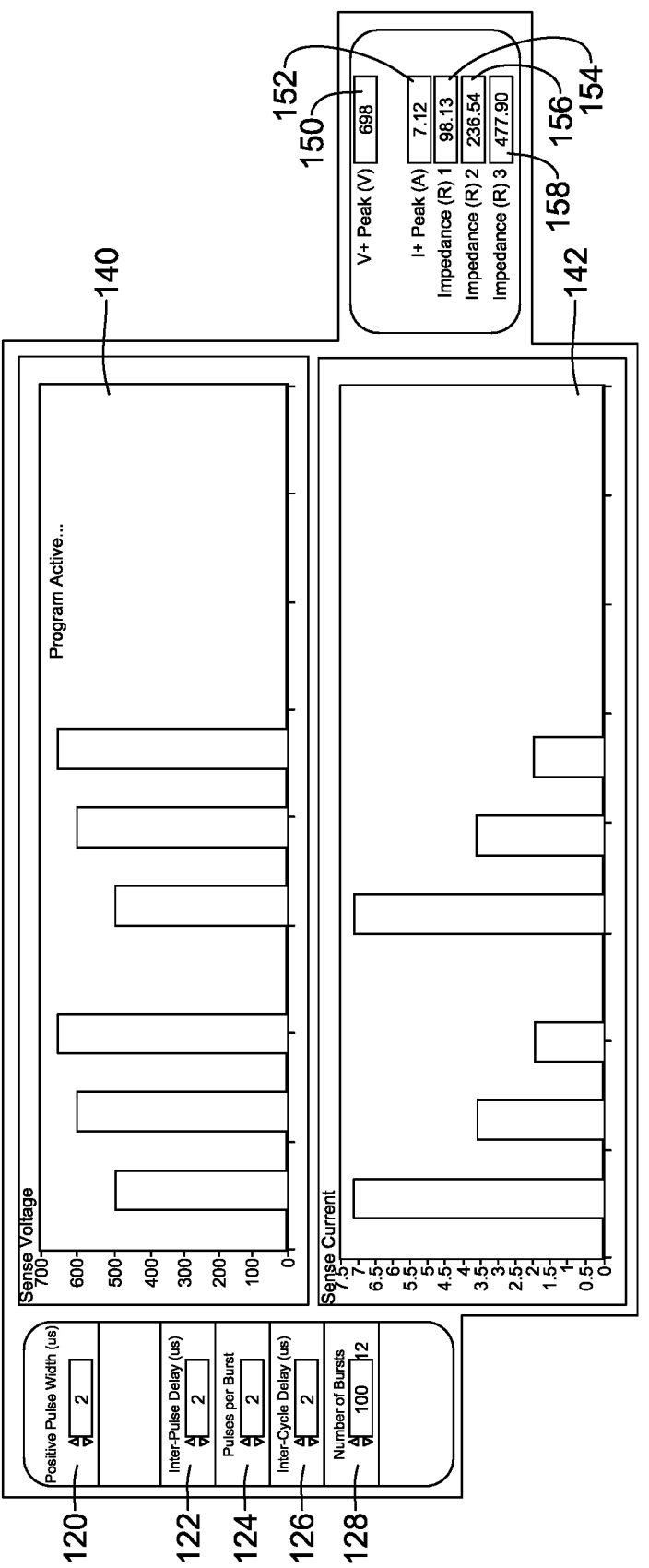

FIGS. 4A-4C illustrates portions of a display having each of programmed parameters and the reporting of output voltage and current, and is highlighted as area 4 in FIG. 1. The reported information varies depending on the waveform type, with FIG. 4A representing a monophasic output, FIG. 4B representing a biphasic output, and FIG. 4C showing a three-electrode rotating output.

A voltage controlled output is shown in the illustrative example. For this example and all others herein, current control or power control may be used instead. Such systems may deliver constant voltage, current or power, in some examples, though any of voltage, current or power can be controlled in a non-constant fashion instead, if desired. For example, a ramped output may be generated. In some example's outputs can be generated from charged capacitors in a manner that allows the output voltage to droop, degrade, or decay over time as the charged capacitors are at least partly discharged during therapy output. The displays illustrated may be adjusted for current or power control and/or for displaying using units of current, power, energy, voltage, and/or impedance, in other examples.

Starting with FIG. 4A, the user interface for a monophasic output shows, during therapy, pulse width 40, pulses per burst 42, intercycle delay 44 and the number of bursts to deliver 46. In a triggered mode, these parameters will determine what therapy is delivered to the patient in response to each triggering event. For example, if the triggering event is a detected cardiac cycle R-wave, one burst is delivered after each R-wave detection, with the burst having the number of pulses defined at 42, the pulses being separated in time by the intercycle delay 44. If a non-triggered therapy output is defined, an interburst delay may be defined as well.

A graphical display of a selected burst delivery is shown at 50, with the generated voltage shown for each of the output pulses in the burst. In the lower box 52, the sensed current for each pulse is shown along the same timeline as the voltage display at 50. In this example the upper box shows voltage and the lower box shows current; in other examples one box may show any of voltage, current, power, or impedance, while the other box may show a different one of voltage, current, power or impedance. In some examples, the values shown may vary within the pulse width to account for changes in the current, voltage, impedance or power during the duration of the pulse. In some examples, the height of each pulse may represent an initial value, an average value, a mid-pulse value, or an end-of-pulse value for the reported or measured parameter.

The display of FIG. 4A includes on the far right reporting of the peak voltage 60, peak current 62, and peak impedance 64. In this example, the reported peak voltage 60 is that which is delivered within the tissue and is calculated by measuring the delivered current output 62 and then using the known impedances of the signal generator and probe to subtract voltage loss that occurs before the signal is delivered. Likewise, the calculated peak impedance 64 can be determined using the current output to calculate total impedance and then subtracting the known impedances of the signal generator and probe. To facilitate such calculations, probe impedance may be tested prior to delivering therapy using a test apparatus, or probe impedance may be determined by the use of a look-up table based on the type of probe in use. The type of probe in use may be determined by user input or may be determined by the use of a smart-probe interface on the ports of the signal generator, which could identify the type of probe by having the probe include a specialized port interface unique to the probe type, or by including an RFID tag on the probe and an RFID reader in/near the port for receiving the probe on the signal generator, for example.

FIG. 4B shows another interface, here tailored for a biphasic mode. On the right side, the therapy delivery parameters are now more fully populated, including each of a positive pulse width 70, negative pulse width 72, interpulse delay 74, pulses per burst 76, intercycle delay 78, and number of bursts. In the example, the signal output would be a first, positive pulse phase with a pulse width defined at 70, followed by an interpulse delay period defined at 74, followed by a negative pulse phase of opposite polarity to the positive pulse phase having the pulse width defined at 72, followed by an intercycle delay defined at 78. That sequence would be repeated by the number of pulses per burst defined at 76 to complete each burst. As before, the number of bursts to deliver indicates a triggered delivery. If a non-triggered therapy output is defined, an interburst delay may be defined as well; during triggered therapy there is no need for an interburst delay as that duration is replaced with the trigger.

In an alternative, multiple bursts may be delivered in response to one triggering event, such as 2, 3, 4 or more bursts, and an interburst delay may be defined for a triggered therapy in such an example. The quantity of bursts that may be delivered in response to a triggering event may be set to maximize the use of a defined therapy window that follows a triggering event. For example, if the occurrence of an R-wave or other cardiac signal is used as a trigger, and the window for therapy is selected as the S-T segment, a window for therapy may be in the range of 5 to 150 milliseconds, depending on heart rate. If a burst comprises 100 biphasic cycles, with each cycle consuming 8 microseconds, then the burst can be completed in under 1 millisecond, allowing several bursts to be delivered in a single therapy window. Thus, the number of bursts to be delivered, in a triggered therapy window, as well as an interburst delay, may also be included as programmable parameters in some examples. Such parameters may be displayed below element 80.

The user interface shows the voltage output at 90 in this example for a given burst. Impedances of each delivered phase of the burst are graphically shown at 92 along the same timeline as used at 90. The numerical results are shown on the right, with the positive peak voltage 100, negative peak voltage 102, positive peak current at 104, and impedance at 106. If desired, negative peak current may also be shown. The impedance shown at 106 is for the first positive phase output of the sequence; in other examples, a negative phase impedance may be shown as well.

FIG. 4C shows another interface, this time tailored to a three-electrode rotating therapy configuration. In this configuration, three output pulses are delivered in a series, each using a different selection of electrodes than the immediately preceding pulse. Tables for illustrative three-electrode rotating therapy outputs are shown above. In the example of FIG. 4C, the pulse delivery parameters are shown on the left side, with the pulse width of each of the output pulses selected/ displayed at 120, the inter-pulse delay at 122, the number of pulses in each burst at 122, the intercycle delay at 126, and the number of bursts to deliver at 128. In this example, each of the pulses is delivered using the same output voltage, pulse width, and interpulse delay period. The example shown would deliver three pulses in sequence, twice, within each burst.

The graphic representations 140 and 142 show the sensed delivered voltage of each pulse at 140, and the current delivered at 142. In this example, the voltages shown at 140 are corrected to account for system and line losses in the output voltage and so, as can be observed, delivered current for the first of each set of three pulses is higher, causing larger line losses and a lower delivered voltage, than the other two pulses in the sequence. By illustrating the voltage and current for each delivered pulse on one timeline, the operator can see the differences in outputs for each of the different therapy output electrode combinations.

On the far right, additional details are shown in text form, with the peak voltage for the first pulse noted at 150, the peak current of the first pulse at 152, and the impedance of each pulse shown at 154, 156, 158. Other selections of parameters to show may be selected/displayed in other embodiments. In one example, the text box may show all three peak, average, or minimum voltages, current, or impedances of the delivered output, either as a set of 9 values in table form, or in a fashion allowing a user to cycle through the set of parameters by tapping an icon or other actuation.

Figure 4D:
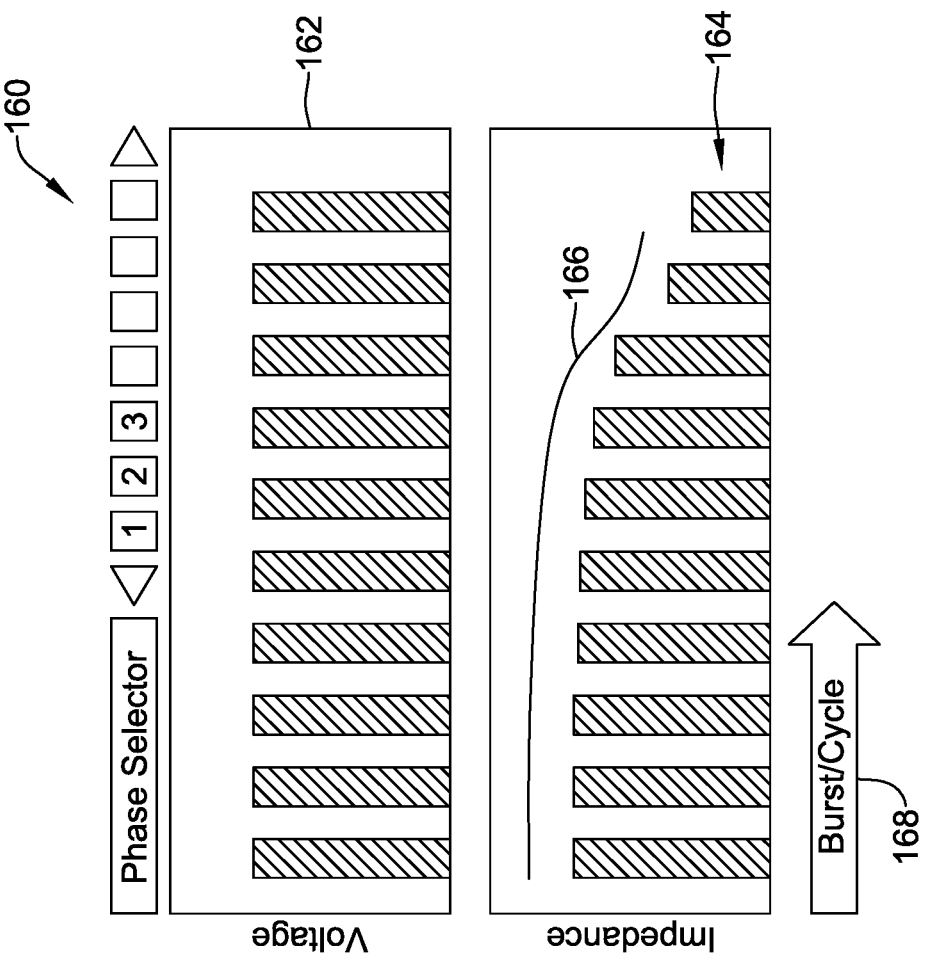

FIG. 4D shows another alternative, here allowing a user to select a particular pulse out of a multiphasic therapy to monitor the voltage and/or impedance over time using a selector or slider as shown at 160. In this example, the user is provided with the option to select a particular phase or pulse of a multiphasic therapy output along tracker 160. The example shown allows the user to pick any of the 1$^{st}$, 2$^{nd}$ or 3$^{rd}$ pulse of a triphasic output, such as that shown in FIG. 4C; more or fewer phases may be used in a particular therapy and the interface at 160 may adjust to the number of phases in use. The delivered voltages are shown at 162; in this example, the output (selected) voltage, without correction for line losses, is shown at 162. Sensed impedance is shown in the lower chart at 164, with the Y-axis of the two charts 162, 164 being based on the delivered burst/cycle, rather than using time along the Y-axis as is used in other examples.

By selecting one of the phases to highlight, the operator can see and understand how impedance is changing for a particular combination of electrodes and/or polarity. If desired, a trendline 166 may be shown. In general, the impedance in a tissue region goes down as ablation therapy progresses, due to breakdown of cellular membranes and the release of intra-cellular fluid, which reduces impedance in the tissue volume. A trend of impedance dropping over time, as shown, suggests that therapy is progressing well in the particular volume. The operator may select to reduce the applied voltage, or omit the particular phase of therapy, as the impedance drops to prevent excess current from flowing and potentially causing undesired ablation away from the target, such as by the transmission of excess thermal energy due to increasing current flow.

In another example, the electrosurgical generator may be configured to modify therapy parameters in response to the impedance. For example, as impedance goes down over time, the system may automatically reduce the issued therapy signal amplitude, to avoid excess current and heating as therapy progresses.

Figure 5A:
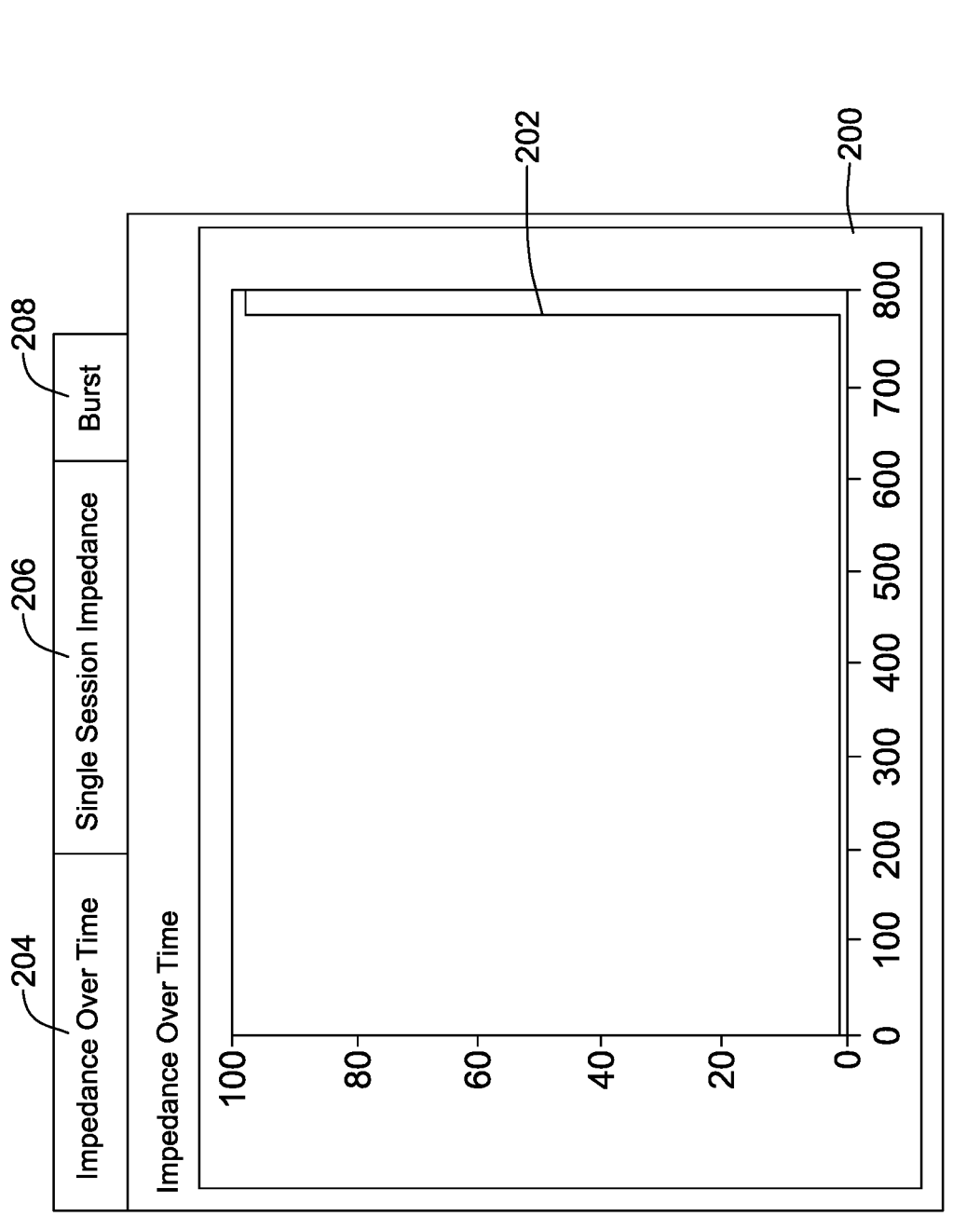
Figure 5B:
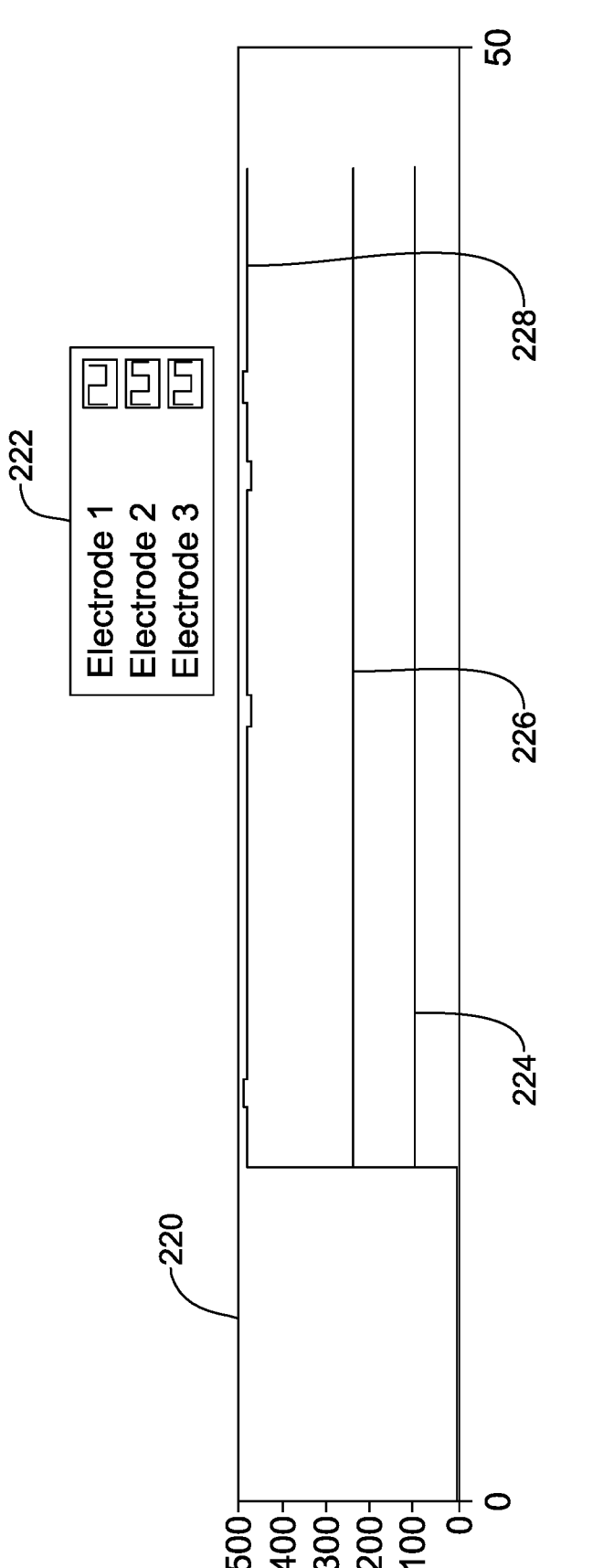

FIGS. 5A-5B shows graphical illustration of impedances corresponding to Area 5 of FIG. 1. In one example, shown in FIG. 5A, impedance for monophasic or standard biphasic outputs is shown on a graph at 200, with a line for the impedance at 202. Here, the impedance of a single pulse is shown. The example interface allows the user to select among impedance over time 204, single session impedance 206, and burst impedance 208, with each showing a different set of details. Impedance over time 204 may display impedance from a plurality of therapy "sessions" each comprising a defined number of bursts or duration of therapy. Impedance in a session 206 may show the impedance during the course of a single session having a defined quantity of bursts or duration of therapy. Impedance for the burst 208 may show impedance for several individual pulses delivered within a burst.

FIG. 5B shows another example, this time for a multiple pulse or phase output. In this example, the impedances across each of a plurality of electrode combinations are shown, corresponding, for example, to a three electrode rotating therapy. In this example, a graphic display 220 shows the impedance for each of three different electrode combinations on the same vertical scale. The Y-axis here is shown in terms of time, but the start time for each of the plurality of pulses is aligned. A key 222 uses different patterns and/or colors for each of the plurality of electrode combinations, with the pulses shown in the graphic display at 220 as lines 224, 226, 228. More or fewer pulses may be shown.

Figure 6:
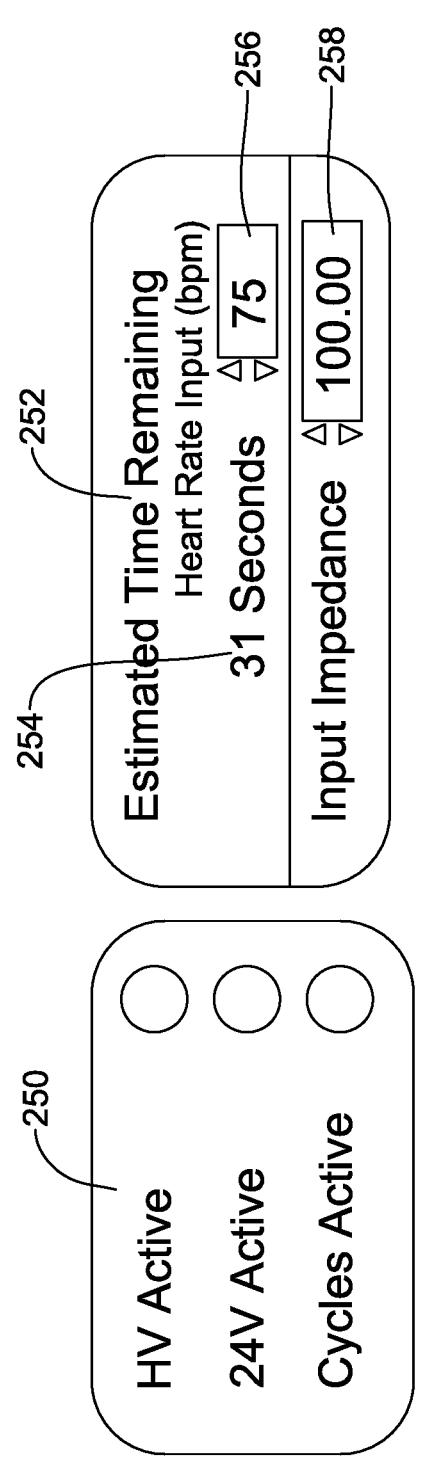
Figure 15:
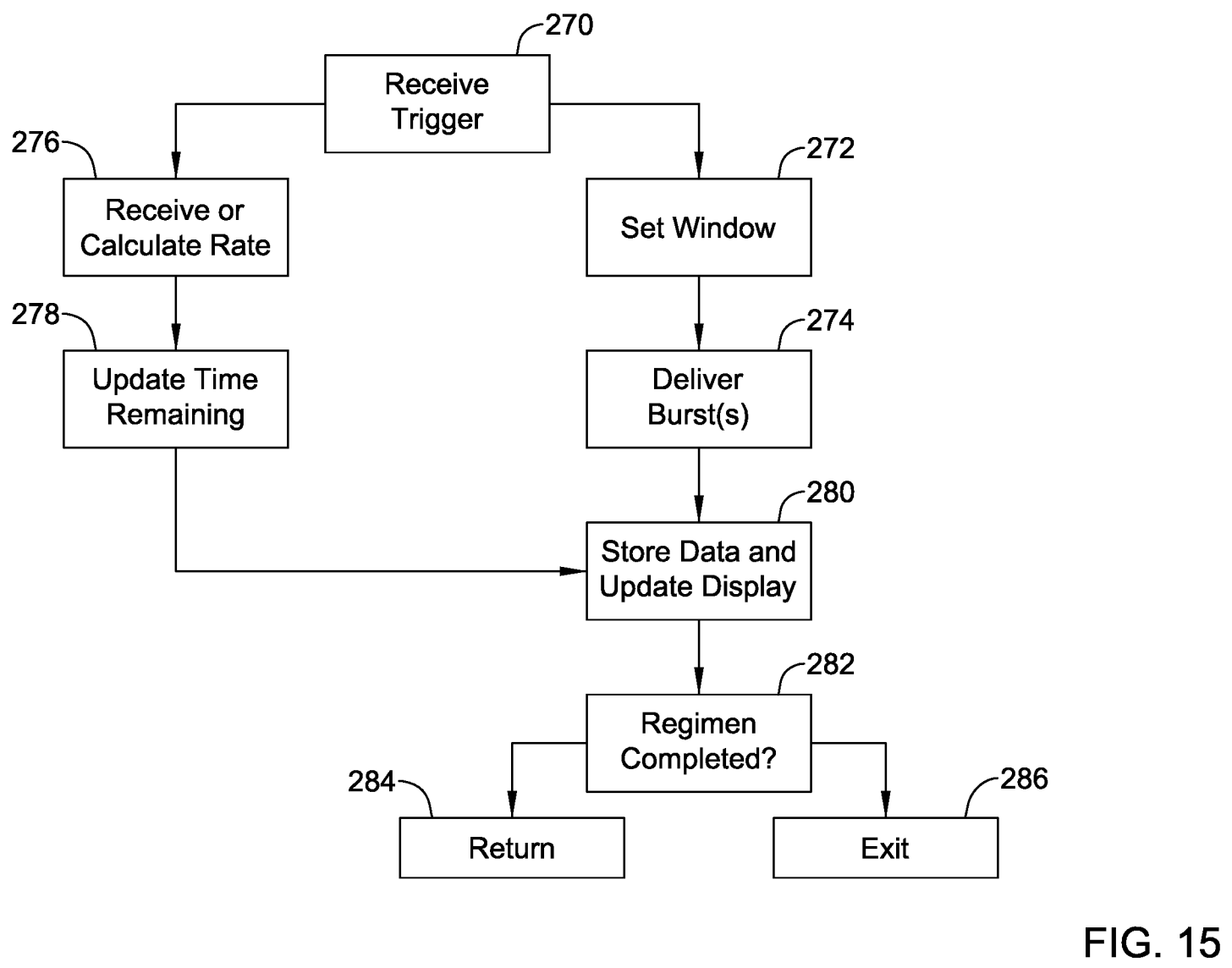

FIG. 6 illustrates a graphic display showing system status and time remaining for a therapy regimen, corresponding to area 6 of FIG. 1. A first area 250 displays the status of the electrosurgical apparatus, including whether the high voltage circuitry is active ("HV Active"), whether control circuitry is active ("24V Active"), and whether the device is engaged in issuing therapy cycles ("Cycles Active"). In another region 252, the estimated time remaining is illustrated, as well as the trigger rate (here, a cardiac rate), with the time remaining at 254 and the heart rate at 256. FIG. 15 shows an illustrative method/process for calculating time remaining. The input impedance is illustrated at 258 as well and represents the line or system impedance that will apply to output currents, which is used to calculate the difference between voltage as applied the tissue and the voltage generated by the high voltage power source of the electrosurgical apparatus.

The value at 258 may be entered by an operator, or it may be calculated using known capabilities of the electrosurgical apparatus and known characteristics of a probe used with the electrosurgical apparatus. Characteristics of the probe may be determined from a look-up table, using, for example, model or serial numbers of the probe entered by a user, or, if a smart-port/probe configuration is used, by reading such information from the probe itself. In some example, characteristics of the probe may be entered manually or stored in the memory of the electrosurgical apparatus.

Turning now to FIG. 15, a method of therapy delivery with tracking and updating time remaining is illustrated. This may be referred to as a timing means for calculating remaining time. FIG. 15 illustrates a process that may be stored as a set of instruction for operating, at least in part or integrated into a larger process, the electrosurgical apparatus. Here, a triggering signal is received at 270, which may be, for example, a cardiac signal or any other signal useful for determining when to deliver therapy, such as a temperature sensor output used to ensure that the tissue a probe is in or adjacent to remains in a desired temperature range. In one branch of the process, therapy delivery occurs by setting a window 272 relative to the triggering signal and delivering one or more bursts of therapy as indicated at 274. In the other branch, a rate at which the triggering event(s) are occurring is received along with the triggering signal (such as when a cardiac monitor provides both a calculated cardiac rate and a cardiac trigger signal), or the rate of triggering event being received is calculated, as indicated at 276. The time remaining is then calculated by taking the rate, whether calculated or received, multiplied by the number of bursts that remain to be delivered, as indicated at 278. The delivery of the bursts and the recalculated time remaining are then used at block 280, where data related to one or more of the delivered therapy, triggering event and rate are stored in a memory, and the display of information to the user is updated. The display update may include updating the displayed voltage, current and/or impedance information described both above and below. The method next determines whether the therapy regimen has been completed, as indicated at 282, and either returns 284 to block 270 to await a next trigger, or exits at 286.

Figure 7:
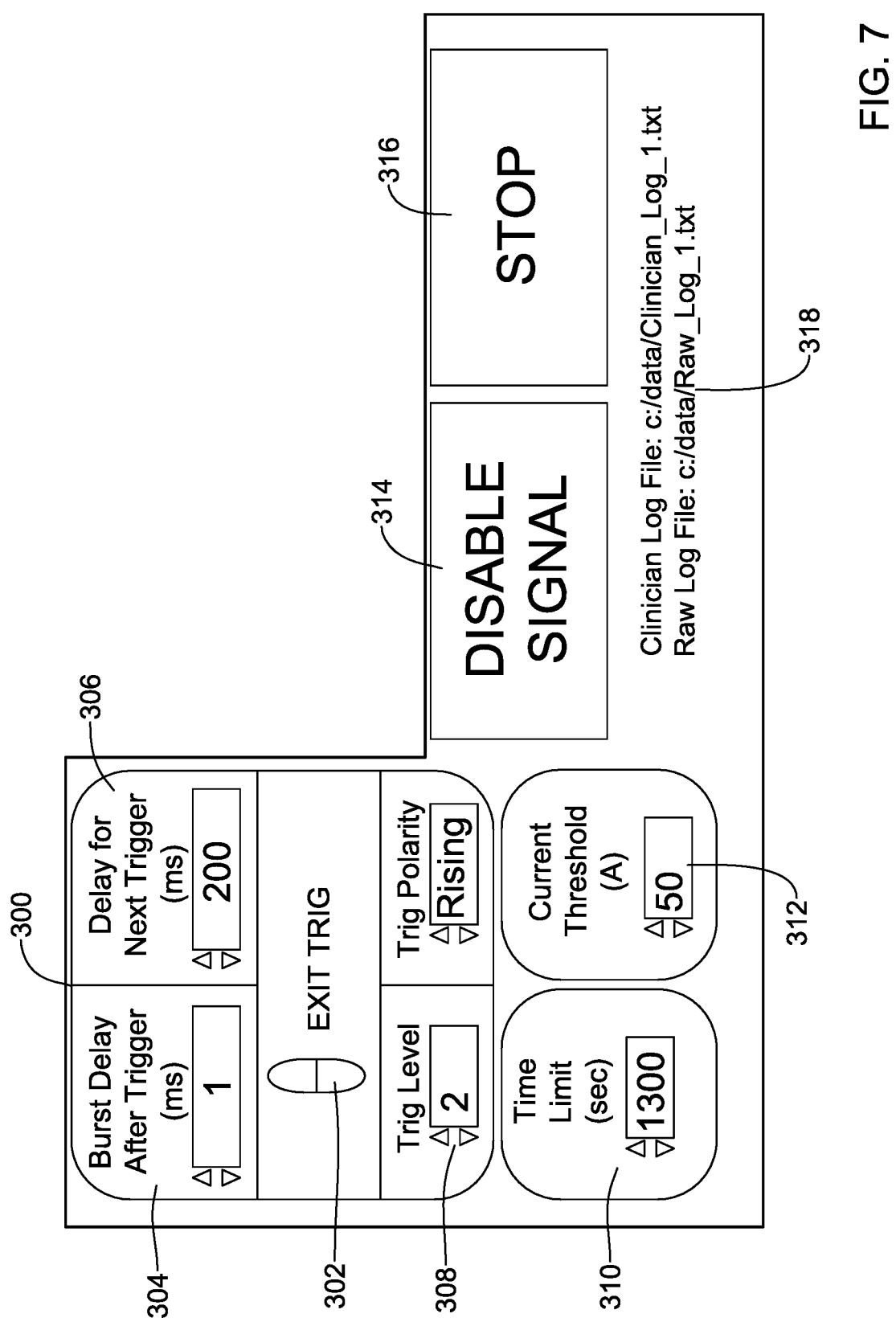

FIG. 7 illustrates a graphic display showing trigger parameters, safety limits and safety controls for an electrosurgical signal generator, and corresponds to area 7 of FIG. 1. In the illustrative example, the graphic display shows trigger-related information and controls at 300. The use of an external trigger can be enabled or disabled by a toggle icon at 302. Details of the trigger implementation may include a delay following the trigger signal at 304, a minimum delay period 306 before a next trigger will be recognized at 306, and parameters of the trigger including signal strength and polarity controls 308, which may allow the user to select parameters related to the cardiac or other signal that is being tracked. The user can set, for example, the delays defined at 304 and/or 306, as well as the type of trigger (rising, falling, peak, etc.) and trigger level 308. In other examples, the controls at 308 may be omitted, and the cardiac signal detection algorithm of a cardiac monitor used to issue the trigger signal may be relied upon instead. In still other examples, a temperature trigger may be used by setting a maximum temperature at which therapy can be initiated, for example.

The system may include automated adjustment of trigger parameters if desired. For example, the system may automatically adjust the burst delay after trigger at 304 to extend the delay at lower pulse rates, or shorten the delay at higher pulse rates, if desired. In some examples, the system may determine a cardiac signal amplitude and use such an amplitude or average amplitude to adjust the trigger level at 308. For example, the system may calculate an average cardiac signal amplitude over time, or a background noise amplitude, and may set the trigger level higher when the average signal amplitude or background noise amplitude are higher, or lower the trigger level when the average signal amplitude or background noise amplitude are lower, to reduce the likelihood of false triggering and/or failure to trigger when appropriate.

Several safety limits are illustrated in FIG. 7 including a time limit for therapy at 310, which ensure the device cannot be left on for an extended period of time; when the time limit expires, the HV system of the electrosurgical apparatus will power down and the user may receive audible and/or visual notifications. A maximum current threshold can be set at 312, as desired, such as by reference to a maximum rating of the probe to be used with the system (in the event of a smartprobe system, the maximum current may be automatically set or limited to a value related to the probe capabilities). An icon for disabling the signal output is provided at 314 and may be used to "pause" therapy delivery until selected a second time. This may be used if it is determined that the probe needs repositioning, or the triggering signal capture device (such as several ECG electrodes) require repositioning, for example. An all stop button 316 is also provided and may initiate complete shutdown of the system, for example, in the event of a system fault.

The display also provides file names for one or more data files that log therapy delivery, as shown at 318. In an example, two log files may be maintained, with one log file accessible to the operator for observing, in simpler form, therapy progress and any events that took place during therapy. This "clinician" log file may contain single or few parameters for the pulses delivered during therapy, such as providing one or more of average, peak, and/or minimum voltage, current, or impedance for representative therapy pulses (i.e., the first pulse of each burst, for a first pulse for each electrode combination used in a burst) or averages across bursts, either generally or broken out for individual electrode combinations/polarities. An "engineering" log file may contain more comprehensive data, such as a point-by-point sampling of voltage, current and/or impedance of each pulse delivered during a therapy regimen, as well as internal values for various components to allow the engineering team to determine both a very detailed therapy output for the regimen, as well as how the electrosurgical apparatus performed during therapy. The engineering log file may contain a representation of the therapy signal, in raw or unprocessed form, or in a compressed format, for example. For example, with a given therapy regimen, the clinician log file may omit information about the droop experienced by the HV signal source during delivery of therapy bursts, while the engineering log file may contain HV signal source data, which can be useful to diagnose performance of the HV circuitry and whether any battery or capacitor elements, switches, etc. need replacement. Any trigger signal information may be included in one or both of the log files. For example, a clinician log file may include data indicating when trigger signals were identified, while the engineering log file may include the captured ECG signal in its entirety (unprocessed or compressed, as desired), to allow an assessment of whether triggering was performed correctly relative to the ECG signal itself.

Figure 8:
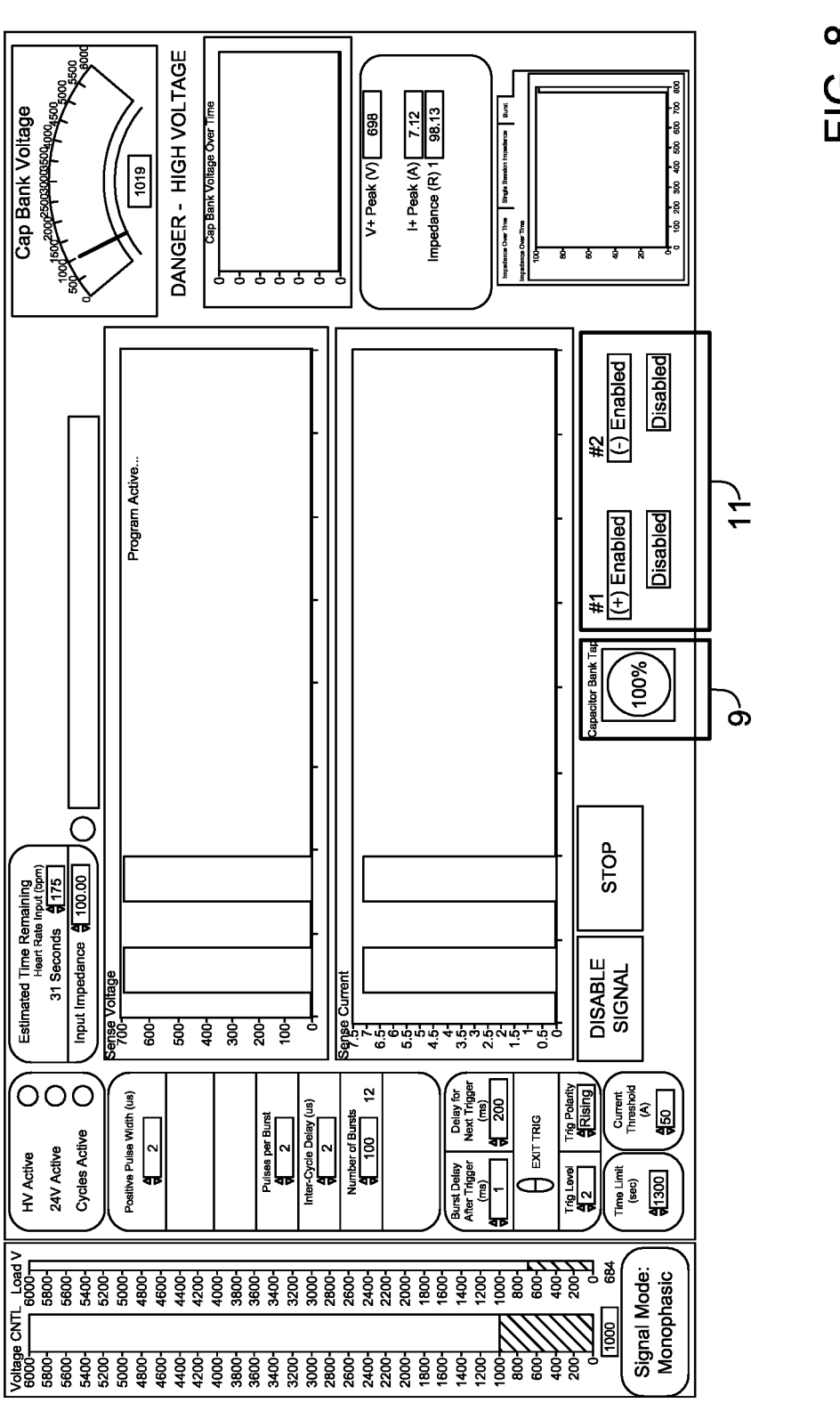
FIG. 8 illustrates another user interface for an electrosurgical apparatus.

FIG. 8 illustrates another user interface for an electrosurgical apparatus. Area 9 illustrates a user-selectable control for automatically reducing the output voltage without interrupting therapy, and is further explained with reference to FIG. 9 and FIGS. 10A-10B. Area 11 shows a simple approach to electrode selection usable in particular with the simplified monophasic or biphasic therapy output configurations of the user interface, and is further explained with reference to FIGS. 11A-11b.

Figure 9:
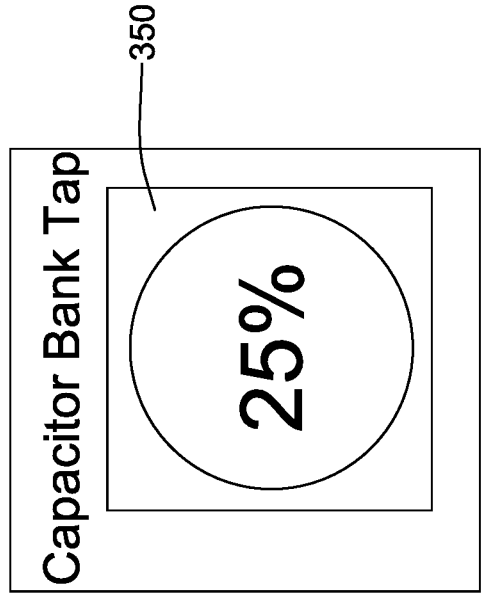
FIG. 9 highlights a feature of a user interface with reference to FIG. 8.
Figure 10A:
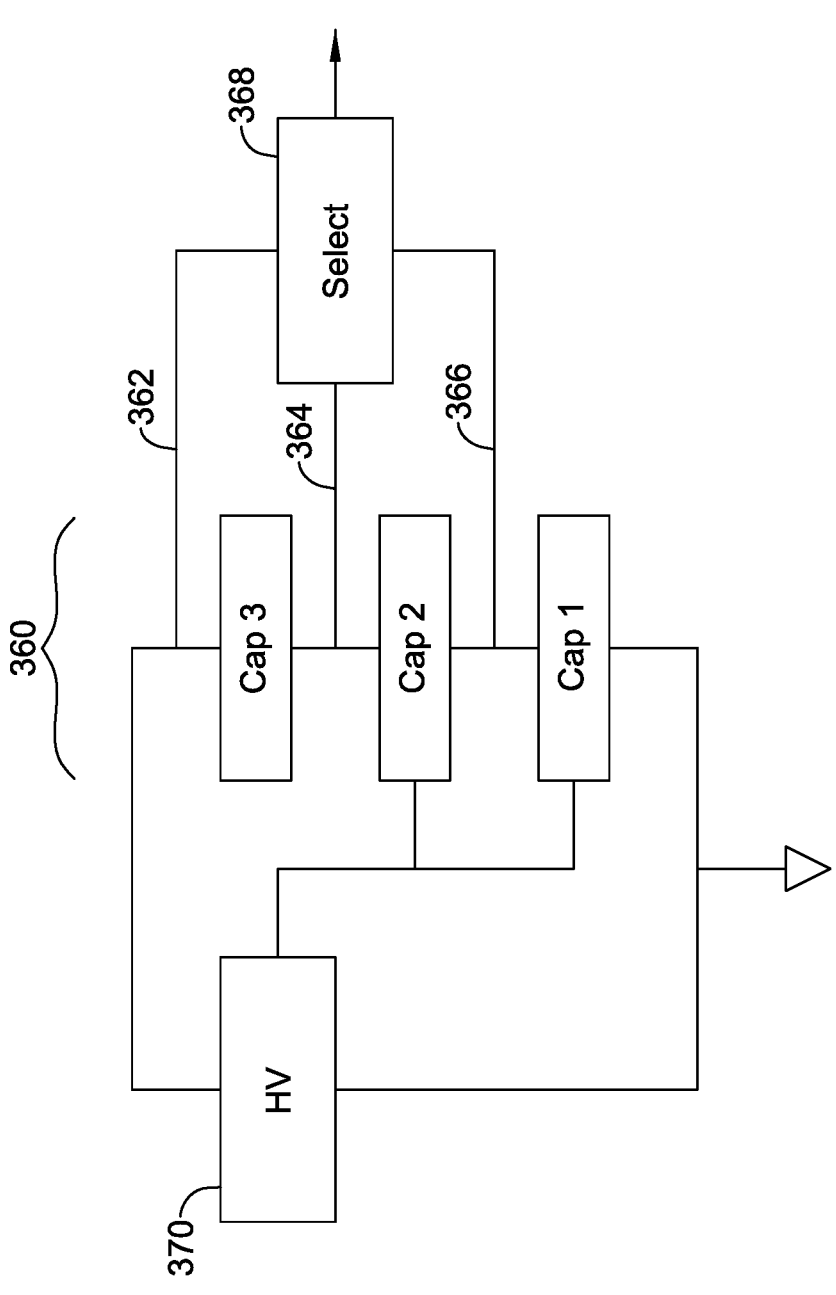
FIGS. 10A-10B show illustrative circuitry facilitating the feature of FIG. 9.

FIG. 9 highlights a feature of a user interface with reference to FIG. 8. In the example, the control is named the "Capacitor Bank Tap" control 350, and allows the user to switch a system output from using a full HV capacitor bank voltage as the output signal control, to using less than the whole bank of capacitors. For example, if four capacitors are provided, the user may tap on the Capacitor Bank Tap to select a tap location chosen from 100% (four series capacitors output), 75% (three of four series capacitors), 50% (two of four series capacitors output) or 25% (one of four series capacitors output). In other examples, different quantities of capacitors may be used to generate other control levels. An example using a capacitor bank tap is shown in FIG. 10A. In an alternative example, the selector here may have a slider bar allowing the user to choose a percentage of the output to use by triggering a step down circuit as shown in FIG. 10B.

Figure 10B:
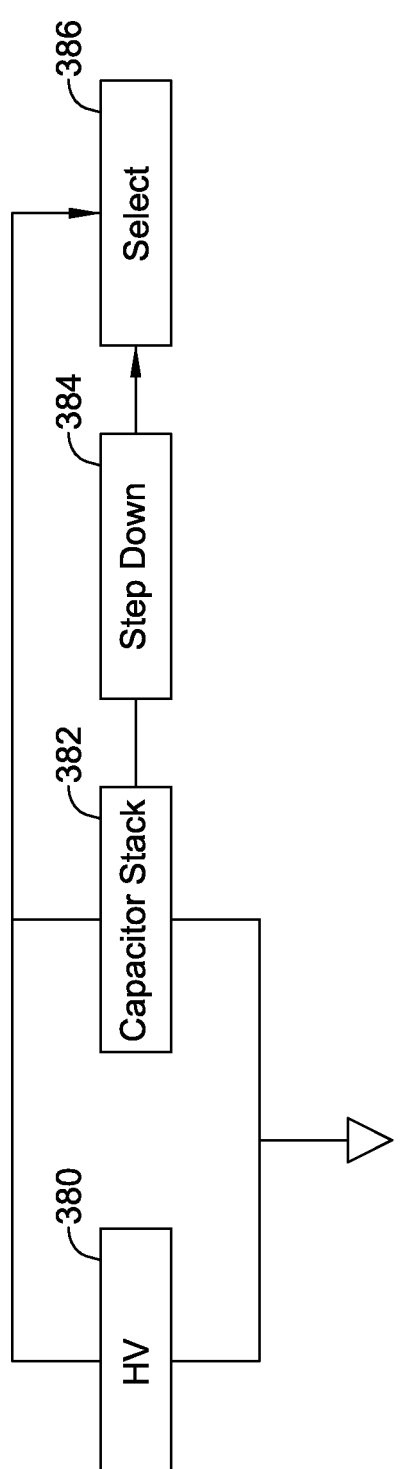

FIGS. 10A-10B show illustrative circuitry facilitating the feature of FIG. 9. Starting with FIG. 10A, an example with a three capacitor bank is shown, with the HV stack shown at 360 and having each of 100% tap 362, 66% tap 364, and 33% tap 366, selectable using a selection block 368, which may be a set of high power switches. With the availability of different output taps on the capacitive circuit, the HV charger 370 may be configured to couple to each capacitor individually. The use of appropriately placed diodes and switches will allow the capacitors to be, in effect, charged in parallel and discharged in series, which in turns allows the capacitors to be kept equally charged so that the use of a subset of the capacitor stack 360, omitting one or more capacitors, will not create an imbalance among the capacitors, distorting the tap selection math. For example, a triple-tapped transformer, gated in a flyback transformer configuration, may be used to charge the three capacitors in the stack 360 using a primary phase to store energy in the transformer and a secondary phase to discharge the stored energy to the capacitor stack 360. When one capacitor has less voltage stored than the other two capacitors, the current from the transformer will be directed to the capacitor having the lowest voltage as it will present the least impedance to the secondary phase discharge current.

While a single HV charger 370 is shown, in other examples, a plurality of capacitors can be provided with two or more HV chargers 370 configured to charge individual ones, or combinations of two or more, capacitors 360. Rather than arrangement in a stack, the capacitors can be provided separately, each referenced to ground as desired. Arrangements of additional switches may be provided in the selection block 368, and/or between the individual capacitors and the HV charger 370 and/or ground, to enable flexible use of the capacitors in any arrangement desired.

FIG. 10B shows another example. Here, an HV charging circuit 380 is coupled to a capacitor stack 382. A step down circuit 384 can be selectively activated to provide a reduced voltage from the capacitor stack to a selector 386, which is used to route either the complete capacitor stack voltage to the therapy outputs, or the stepped-down voltage from the step down circuit 384. A hybrid circuit may use both a step down 384 and a selectable capacitor stack tap to provide reduced outputs with precision, while reducing the amount of voltage the step down circuit 384 has to handle.

In some examples, additional arrangements of switches may be used to allow capacitors to be linked together in additional ways. For example, a set of three capacitors can be used and linked together with two capacitors in series, charged using a first HV charger 380, and a third capacitor in parallel with the two capacitors and charged using a second HV charger 380. The combination of two capacitors in series, with a third capacitor parallel to the first two capacitors, would allow a tailored output pulse of higher capacitance than if the third capacitor is omitted, flattening the output pulse. With the same elements, the three capacitors may instead be linked together in series, yielding a lower capacitance to the total stack and causing the output therapy as delivered to have a greater slope when therapy is delivered.

In another example, an electrosurgical generator may have 4, 6, or more high power capacitors adapted for therapy delivery purposes. The capacitors can then be divided into two or more groups, with each group charged to a selected power level sufficient to provide a burst of therapy, with or without a desired degree of decay within individual pulses or across a burst of therapy. The groups of capacitors may be used in an alternating fashion, such that as a first group of capacitors is used to deliver a first therapy burst, a second group is charged by the HV charger. A second therapy burst can then be delivered using the second group of capacitors, while the HV charger recharges the first group of capacitors.

Periodic tests may be run on the capacitors to ensure that each one is operating properly. If a capacitor is found to be no longer operating within set bounds, switches coupling that capacitor to the rest of the system may be opened until maintenance is performed, effectively locking out the non-conforming capacitor. A flag or alert to the user may be set if a capacitor is not functioning correctly. A periodic test may be, for example, performed by charging a capacitor to a predetermined level and monitoring the voltage stored on the capacitor for a period of time to determine a leakage rate associated with the capacitor, followed by discharge of the capacitor into a known load (a passive resistor, for example) to calculate the internal impedance of the capacitor and/or its effective capacitance. The calculated leakage, internal impedance, and effective capacitance can then be used to determine if the capacitor is operating within functional boundaries. Such tests may be performed as part of an initialization, turn-on, and/or warmup sequence for an electrosurgical generator.

Figure 11A:
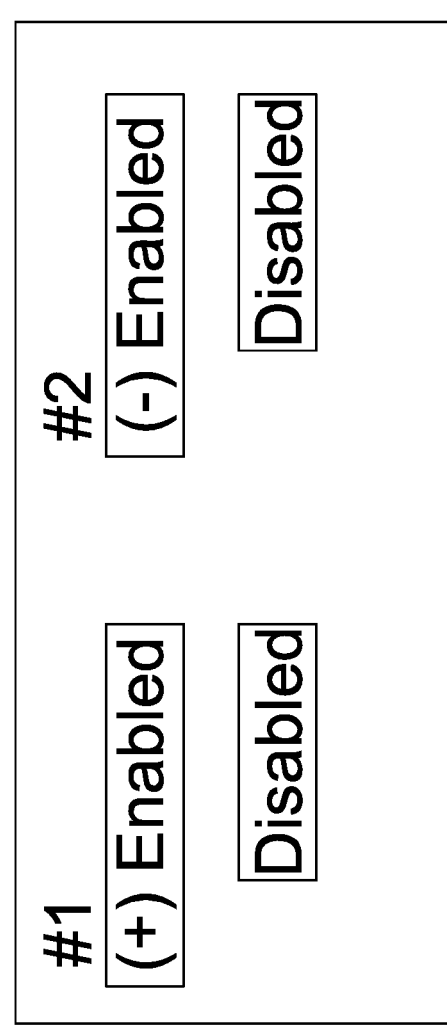
Figure 11B:
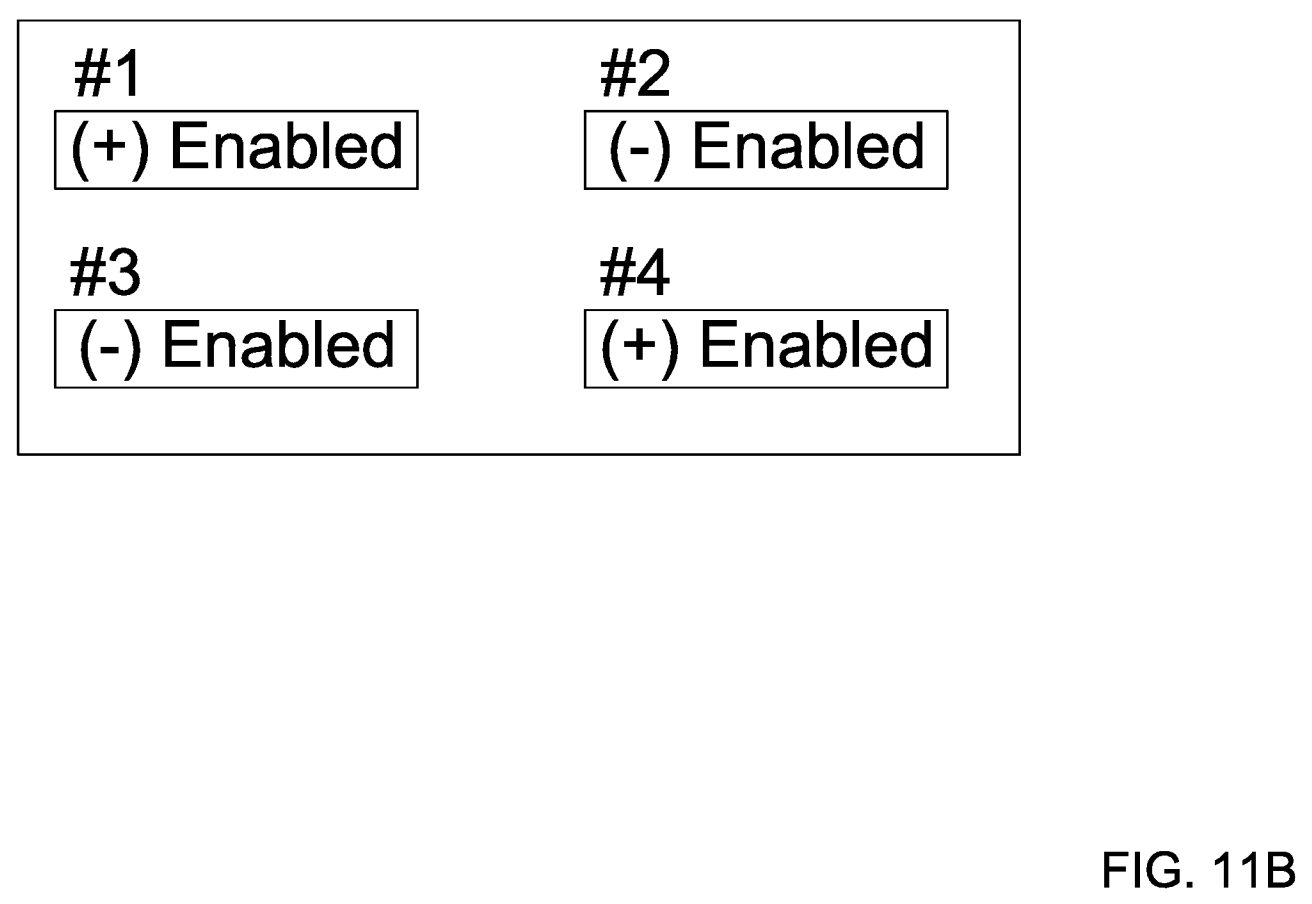

FIGS. 11A-11B highlight features of a user interface with reference to FIG. 8. Here the user is provided, on the graphical display, the option to select and identify individual electrodes of a probe as anodes and cathodes, or disabled. For example, a single pair of anode and cathode may be selected as shown at FIG. 11A, or a setup of two anodes and two cathodes may be used as shown at FIG. 11B. Unbalanced combinations may be used, if desired, with two or three anodes and one cathode, or two or three cathodes and one anode, instead.

Figure 12:
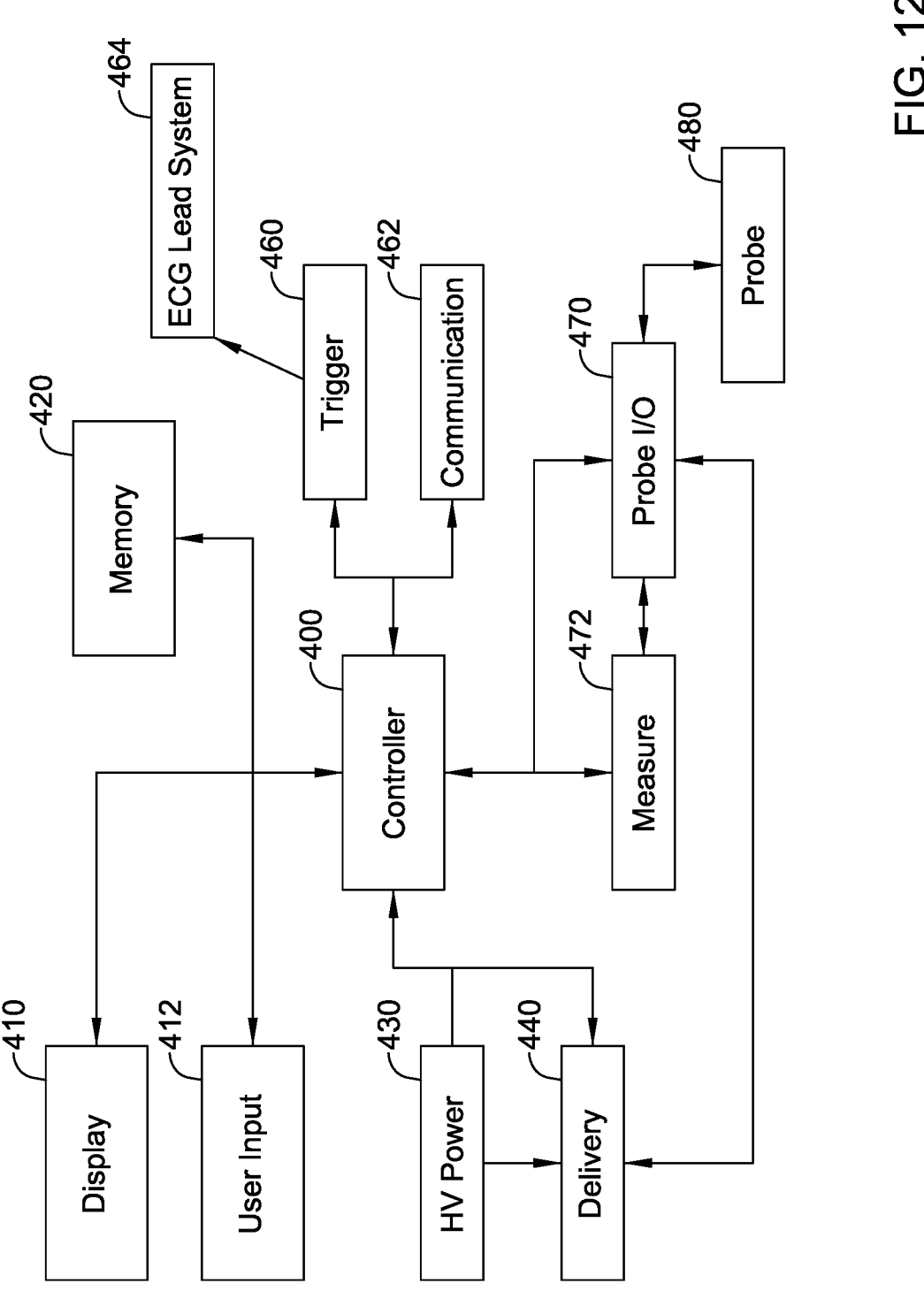
FIG. 12 illustrates in block form an electrosurgical apparatus.

FIG. 12 illustrates in block form an electrosurgical apparatus. The apparatus contains a controller 400 which may be, for example, a state machine, a microcontroller or microprocessor adapted to execute programmable instructions, which may be stored in a memory 420 that can also be used to store history, events, parameters, sensed conditions, alerts, and a wide variety of data such as template programs, information related to probes 480, and the like. The memory 420 may include both volatile and non-volatile memory types, and may include a port for coupling to a removeable memory element such as an SD card or thumb drive using a USB port. The stored instructions can be selected, configured or adjusted by a user to define, for example and without limitation, therapy characteristics including pulse width, pulse amplitude, phase details (number of phases and type, as well as interphase delay), pulse and burst repetition rates, pulse shape, pulse quantity in each burst, burst repetition rate, and pulse type (current, voltage, power, energy controlled) and shape (square wave, decaying, ramped, etc.) The stored instructions may also define how pulses change, if at all, during a burst (such as by increasing or decreasing amplitude from a first pulse of a burst to the second and subsequent pulses).

The controller 400 is coupled to a display 410 and user input 412. The display 410 and user input 412 may be integrated with one another by including a touchscreen. The display 410 may be a computer screen and/or touchscreen and may also include lights and speakers to provide additional output statuses or commands, verbal prompts, etc. The user input 412 may include one or more of a keyboard, a mouse, a trackball, a touchpad, a microphone, a camera, etc. Any inputs by the user may be operated on by the controller 400. The controller 400 may include one or more application specific integrated circuits (ASICs) to provide additional functionality, such as an ASIC for filtering and analyzing an ECG for use as a trigger signal, or analog to digital conversion circuits for handling received signals from a probe apparatus.

The controller 400 is also coupled to an HV Power block 430, which may comprise a capacitor stack or other power storage apparatus, coupled to a charger or voltage multiplier that provides a step up from standard wall power voltages to very high powers, in the hundreds to thousands of volts. A therapy delivery block 440 is shown as well and may include high power switches arranges in various ways to route high voltages or currents from the HV power 430 to a probe input/output (Probe I/O) 470, which in turn couples to a probe 480. In some examples, the HV power block 430 and Delivery block 440 may incorporate circuitry and methods described in U.S. patent application Ser. No. 16/818,035, filed Mar. 13, 2020 and titled WAVEFORM GENERATOR AND CONTROL FOR SELECTIVE CELL ABLATION, the disclosure of which is incorporated herein by reference.

The Probe I/O 470 may include a smart probe interface that allows it to automatically identify the probe 480 using an optical reader interface (barcode or QR code) or using an RFID chip that can be read via an RF reader, or a microchip that can be read once the probe 480 is electrically coupled to a port on the Probe I/O 470. A measuring circuit 472 is coupled to the Probe I/O 470, and may be used to measure voltages, currents and/or impedances related to the probe, such as measuring the current flowing through a connection to the probe 480, or the voltage at an output of the Probe I/O 470. The Probe I/O may comprise electrical couplings to the Probe 480 for purposes of therapy delivery, or for sensing/measurement of signals from the Probe 480, using for example sensing electrodes or sensing transducers (motion, sound, vibration, temperature or optical transducers, for example), as well as an optical I/O if desired to allow the output or receipt of optical energy, such as using optical interrogation of tissue or issuing light at therapeutic levels or even at ablation power levels. Not all of these options are required or included in some embodiments.

The controller 400 is also coupled to trigger circuitry 460 and/or communications circuitry 462. The trigger circuitry may include, for example, an ECG coupling port that is adapted to receive electrodes or an ECG lead system 464 for capturing a surface ECG or other signal from the patient for use in a triggered therapy mode. A communications circuit 462 may instead be used to wirelessly obtain a trigger signal, either a trigger that is generated externally, or a raw signal (such as an ECG) to be analyzed internally by the controller 400. The communication circuit 462 may include a transceiver having one or more of Bluetooth or WIFI antennas and driver circuitry to wirelessly communicate status, data, commands, etc. before, during or after therapy regimens are performed. If desired, the trigger 460 may have a dedicated transceiver itself, rather than relying on the system communication block 460.

The ECG electrodes, if provided, may be placed on the chest of the patient, for example, in predetermined positions for capturing the patient's cardiac signal. Suitable ECG electrode positions may be those that preferentially capture ventricular activity (the R-wave or ventricular depolarization, associated with what is colloquially known as the heart beat), though in some examples the ECG electrodes may positioned to capture any portion of the cardiac signal, including for example both atrial and ventricular signals. If a communication circuit is used, communication may be to a separate ECG detector. The "ECG detector" may be a device that only senses cardiac signals, or it may be integrated into a cardia pacing unit or a defibrillator device. Any such system that can be used for wired or wireless communication to the trigger circuitry may be used. In some examples, the patient may receive pacing therapy during a therapy session to control heart rate in a predictable fashion, such as by pacing at a rate that exceeds the patient's intrinsic rhythm rate and/or resting heart rate, ensuring predictable cardiac rate and signal characteristics.

The probe 480 may take any suitable form, such as a Leveen needle, or a probe as shown in U.S. Pat. Nos. 5,855,576, 6,638,277, and/or US PG Pat. Pub. No. 2019/0223943, the disclosure of which is incorporated herein by reference, or other suitable ablation designs such as using multiple probes each comprising a needle electrode, either integrated into one structure or separately placed. The probe 480 may include one or more indifferent or return electrodes, such as plates that can be cutaneously placed.

A first illustrative and non-limiting embodiment takes the form of an electrosurgical generator (such as, for example, the generator shown in FIG. 12) comprising: one or more ports adapted to receive one or more electrosurgical probes (such described with respect to block 470), each port comprising at least one contact; a high voltage power source (such as described with respect to block 430); delivery means for selectively routing an output from the power source to selected contacts of the one or more ports (such as the circuitry described with reference to block 440 of FIG. 12); a controller having stored instructions that can be selected, configured or adjusted by a user (such as a controller as shown at 400 in FIG. 12, having access to stored instructions of the memory 420 or accessible using a communications block 462 having, for example, Ethernet, USB, cellular, Bluetooth or WiFi communications capability, to off-device data storage), the stored instructions including at least one instruction set for delivering a therapy regimen, the therapy regimen comprising a series of pulses each having a pulse amplitude and a pulse width, the series of pulses forming a burst, the instruction set defining the pulse amplitude, the pulse width, how many pulses are in each burst, and how many bursts are to be delivered in the therapy regimen and, optionally, a pulse repetition rate or burst repetition rate (Several examples are shown in various figures; without limiting to one example, FIG. 4A shows such a burst in the program block for sensed voltage at 50, in which example there are two pulses in a burst as defined at 40, each pulse having an amplitude and pulse width, with the number of bursts to be delivered at 46); and a user interface having a user operable change means that the user can actuate to modify the pulse amplitude without stopping or interrupting the therapy regimen (such a change means is shown in FIGS. 8-9, with full amplitude delivered as shown at 9 in FIG. 8, and a fraction of the full amplitude delivered when the user interface is actuated as shown in FIG. 9). Additionally or alternatively, the high voltage power source comprises at least first and second capacitors placed in series for purposes of outputting therapy pulses, and stack selection means, wherein the stack selection means is controlled by the user operable change means to include all or less than all of the capacitors in the series for purposes of outputting therapy pulses (FIG. 10A shows this configuration with at least two capacitors, three being illustratively shown, and a stack selection means at 368 to select all or a part of the stack). Additionally or alternatively, the electrosurgical generator of claim 1 wherein the high voltage power source comprises step down means controlled by the user operable change means to route a higher or lower voltage from the high voltage power source to the delivery means. As noted previously, the electrosurgical system may be configured to define, control, and/or display therapy in terms of voltage, current, power, and/or energy, as desired, including, optionally, by the use of constant voltage, power, current, and/or energy therapy delivery.

A second illustrative and non-limiting embodiment takes the form of an electrosurgical generator (such as, for example, the generator shown in FIG. 12) comprising: one or more ports adapted to receive one or more electrosurgical probes (such described with respect to block 470), each port comprising at least one contact; a high voltage power source (such as described with respect to block 430); delivery means for selectively routing an output from the power source to selected contacts of the one or more ports (such as the circuitry described with reference to block 440 of FIG. 12); a controller having stored instructions that can be selected, configured or adjusted by a user (such as a controller as shown at 400 in FIG. 12, having access to stored instructions of the memory 420 or accessible using a communications block 462 having, for example, Ethernet, USB, cellular, Bluetooth or WiFi communications capability, to off-device data storage), the stored instructions including at least one instruction set for delivering a therapy regimen, the therapy regimen defining a multi-polar output sequence in which at least three electrodes are used, with a first selection of the electrodes used to deliver a first pulse and a second selection of the electrodes, different from the first selection of the electrodes, used to deliver a second pulse (FIGS. 1 and 4C each show a three electrode rotating therapy configuration in which groups of three pulses are delivered in sequence using different electrode pairs for each of the three pulses—see FIG. 4C at 140); measurement means for measuring impedance during delivery of a therapy pulse (such as block 472 as described relative to FIG. 12); a user interface configured for displaying therapy delivery parameters during or after generation of the therapy regimen, the user interface displaying the amplitude of the first pulse and the second pulse in a first portion of the user interface and impedance encountered by the first pulse and the second pulse in a second portion of the user interface, to facilitate comparison of the first pulse and second pulse amplitudes and impedances (See FIGS. 1 and 4C, showing a user interface facilitating such a comparison).

Additionally or alternatively to either of the first and second illustrative, non-limiting embodiments, the electrosurgical generator may also comprise a trigger means adapted to sense or receive a representation of a cardiac signal of a patient, the trigger means configured to identify a therapy window for delivery of a burst from within the therapy regimen, wherein the delivery means is responsive to the trigger means to issue a therapy burst (as shown and described with reference to block 460 in FIG. 12).

A third illustrative and non-limiting embodiment takes the form of an electrosurgical generator (such as, for example, the generator shown in FIG. 12) comprising: one or more ports adapted to receive one or more electrosurgical probes (such described with respect to block 470), each port comprising at least one contact; a high voltage power source (such as described with respect to block 430); delivery means for selectively routing an output from the power source to selected contacts of the one or more ports (such as the circuitry described with reference to block 440 of FIG. 12); a controller having stored instructions that can be selected, configured or adjusted by a user (such as a controller as shown at 400 in FIG. 12, having access to stored instructions of the memory 420 or accessible using a communications block 462 having, for example, Ethernet, USB, cellular, Bluetooth or WiFi communications capability, to off-device data storage), the stored instructions including at least one instruction set for delivering a therapy regimen, the therapy regimen comprising a series of pulses each having a pulse amplitude and a pulse width, the series of pulses forming a burst, the instruction set defining the pulse amplitude, the pulse width, how many pulses are in each burst, and how many bursts are to be delivered in the therapy regimen (Several examples are shown in various figures; without limiting to one example, FIG. 4A shows such a burst in the program block for sensed voltage at 50, in which example there are two pulses in a burst as defined at 40, each pulse having an amplitude and pulse width, with the number of bursts to be delivered at 46); a trigger means adapted to sense or receive a triggering signal from a patient, the trigger means configured to identify a therapy window for delivery of a burst defined by the therapy regimen (such as shown and described with reference to block 460 of FIG. 12); and timing means configured to determine time remaining for the therapy regimen comprising rate means for determining a trigger rate using data from the trigger means, and calculating means for determining how much time will be required to complete all bursts of the therapy regimen in light of the trigger rate (the timing means may include a stored instruction set operable by the controller 400 configured to perform as illustrated in FIG. 15 at blocks 276 and 278); and display means for displaying to a user an estimated remaining time as calculated by the timing means (See, for example, FIGS. 1 and 6, with the estimated time remaining shown at 252 and 254 in FIG. 6, details that may be shown at area 6 in FIG. 1).

Additionally or alternatively, the trigger means may use a cardiac signal and comprises a lead system having ECG electrodes thereon for capturing a cutaneous cardiac signal from a patient and a cardiac signal detector for detecting components of the cardiac signal (See FIG. 12, at 464). Additionally or alternatively, the trigger means uses a cardiac signal and comprises or is coupled to a transceiver for receiving a wireless signal from an ECG detector representing a patient's cardiac signal, and a cardiac signal detector for detecting components of the cardiac signal (See FIG. 12, at 460 and 462; as described above, the transceiver of the system communication block 462 may be accessed by the trigger 460, or the trigger 460 may have its own transceiver).

Additionally or alternatively, the user interface allows the user to select a delay period for the trigger means to use to delay the start of a therapy burst relative to a triggering signal (such a user interface is shown in FIG. 7, with the burst delay defined at 304). Additionally or alternatively, the user interface comprises an amplitude display allowing the user to set or adjust therapy amplitude and, in conjunction with the amplitude display, an estimate of the amplitude that will be delivered to tissue between a selected pair of electrodes on a probe coupled to the one or more ports (FIG. 1, area 3; FIG. 3, showing the programmed voltage at 34 and the estimated delivered voltage at 32). Additionally or alternatively, the user interface comprises a waveform selector allowing a user to select from at least biphasic and monophasic waveform types (FIG. 1, area 2; see FIG. 2 showing this structure as a drop-down list).

Additionally or alternatively, the user interface comprises a waveform design tool allowing a user to select electrodes to be used when delivering a pulse, an interval between pulses in each burst, a quantity of pulses to provide in each burst, and a quantity of bursts to deliver (FIGS. 4A-4C each show such user interface tools on the left side of each Figure), and the controller is responsive to the waveform design tool to select, configure, or adjust an instruction set defining the therapy regimen, wherein the waveform design tool allows the user to vary the electrodes from one pulse to the next (FIG. 4C shows such as waveform design tool, as does FIGS. 14A-14B).

Additionally or alternatively, the electrosurgical generator may comprise recording means for storing first and second therapy logs as follows: the first log comprising input and output parameters of therapy as delivered; and a second log recording raw or unprocessed waveforms as delivered to the patient (FIG. 7, element 318 shows the two log file names; associated text above describes such operations). Additionally or alternatively, the user interface comprises a pause button or icon operable to interrupt a therapy regimen without terminating the therapy regimen (Area 7 in FIG. 1; FIG. 7 shows inclusion of two controls at 314 to disable or pause the signal, without cancelling, and a stop button 316 to fully cease therapy and terminate the therapy regimen).

Some examples comprise a system for treating a patient by ablation of a target tissue comprising an electrosurgical generator as in any of the first, second or third illustrative, non-limiting embodiments, and any variant thereof, in combination with a probe configured for use with the electrosurgical generator (FIG. 12, block 480).

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third,"

etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like, stored in a non-transitory medium. Such code can include computer readable instructions for performing various methods. The code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. The above description is intended to be illustrative, and not restrictive. For example, the above-described examples (or one or more aspects thereof) may be used in combination with each other. Other embodiments can be used, such as by one of ordinary skill in the art upon reviewing the above description.

In the Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The following claims are hereby incorporated into the Detailed Description as examples or embodiments, with each claim standing on its own as a separate embodiment. Such embodiments can be combined with each other in various combinations or permutations. The scope of the invention should be determined with reference to the appended claims, along with the full scope of equivalents to which such claims are entitled.

The claimed invention is:

1. An electrosurgical generator comprising:
   at least two contacts for coupling to one or more electrosurgical probes;
   a high voltage power source comprising at least first and second capacitors configured for outputting therapy pulses;
   a delivery circuit comprising a plurality of switches configured to route an output from the power source to selected ones of the at least two contacts, the delivery circuit comprising a stack selector;
   a controller having stored instructions that can be selected, configured or adjusted by a user, the stored instructions including at least one instruction set for delivering a therapy regimen, the therapy regimen comprising a plurality of pulses each having a pulse amplitude and a pulse width, the instruction set defining the pulse amplitude and the pulse width; and
   a user interface having a user operable change tool that the user can actuate during execution of the therapy regimen to modify the pulse amplitude without stopping or interrupting the therapy regimen;
   wherein the stack selector comprises a plurality of switches and has each of a first configuration in which all of the capacitors are used for purposes of outputting therapy pulses, and a second configuration in which less than all of the capacitors are used for purposes of outputting therapy pulses; and further wherein controller is configured to switch the stack selector between the first configuration and the second configuration in response to actuation of the change tool by a user during execution of the therapy regimen.

2. An electrosurgical generator as in claim 1, further comprising a first port having a first one of the at least two contacts, and a second port having a second one of the at least two contacts, wherein:

the first port is adapted to receive a first electrosurgical probe; and the second port is adapted to receive a second electrosurgical probe.

3. An electrosurgical generator as in claim 1, further comprising a port having a first contact and a second contact of the at least two contacts, the port adapted to receive an electrosurgical probe.

4. An electrosurgical generator as in claim 1 wherein the instruction set for delivering the therapy regimen comprises a series of pulses grouped as a burst, the therapy regimen defining how many pulses are in a burst, wherein the controller further comprises an executable triggering instruction set adapted to receive a therapy trigger, identify a therapy window for delivery of a therapy burst from within the therapy regimen relative to the therapy trigger, and instruct the delivery circuit to route a therapy burst to selected contacts of the at least two contacts.

5. An electrosurgical generator as in claim 1 wherein the instruction set for delivering the therapy regimen comprises a series of pulses grouped as a burst, the therapy regimen defining how many pulses are in a burst, wherein the controller further comprises an executable triggering instruction set adapted to identify a therapy trigger, identify a therapy window for delivery of a therapy burst from within the therapy regimen relative to the therapy trigger, and instruct the delivery circuit to route a therapy burst to selected contacts of the at least two contacts.

6. An electrosurgical generator as in claim 1 wherein the instruction set for delivering the therapy regimen comprises a series of pulses grouped as a burst, the therapy regimen defining how many pulses are in a burst, further comprising a trigger circuit adapted to sense a representation of a cardiac signal of a patient, identify a therapy window for delivery of a therapy burst from within the therapy regimen, and instruct the delivery circuit to route a therapy burst to selected contacts of the one or more ports.

7. An electrosurgical generator as in claim 1 wherein the instruction set for delivering the therapy regimen comprises a series of pulses grouped as a burst, the therapy regimen defining how many pulses are in a burst, further comprising a trigger circuit adapted to receive a representation of a cardiac signal of a patient, identify a therapy window for delivery of a therapy burst from within the therapy regimen, and instruct the delivery circuit to route a therapy burst to selected contacts of the one or more ports.

8. A system for treating a patient by ablation of a target tissue comprising an electrosurgical generator as in claim 1, and a probe configured for use with the electrosurgical generator.

9. A method of operating an electrosurgical generator, the electrosurgical generator having at least two contacts for coupling to one or more electrosurgical probes, a high voltage power source comprising at least first and second capacitors configured for outputting therapy pulses, a delivery circuit comprising a plurality of switches configured to route an output from the power source to selected ones of the at least two contacts, a controller having stored instructions that can be selected, configured or adjusted by a user, the stored instructions including at least one instruction set for delivering a therapy regimen, the therapy regimen comprising a plurality of pulses each having a pulse amplitude and a pulse width, the instruction set defining the pulse amplitude and the pulse width, and a user interface;

the method comprising:

receiving an indication to start the therapy regimen;

displaying, on the user interface, a user operable change tool, the user operable change tool configured to be responsive to user actuation during execution of the therapy regimen to modify the pulse amplitude without stopping or interrupting the therapy regimen, wherein the delivery circuit includes a stack selector, the stack selector having a plurality of switches and each of a first configuration in which all of the capacitors are used for purposes of outputting therapy pulses, and a second configuration in which less than all of the capacitors are used for purposes of outputting therapy pulses, the stack selector responsive to the user operable change tool;

with the user operable change tool accessible on the user interface, initiating the therapy regimen using a first therapy amplitude by setting the stack selector to the first configuration;

receiving, at the user interface, an actuation of the user operable change tool; and continuing the therapy regimen using a second therapy amplitude, without stopping or interrupting the therapy regimen, by setting the stack selector to the second configuration.

10. A method as in claim 9, wherein the controller further comprises an executable triggering instruction set adapted to receive a therapy trigger, identify a therapy window for delivery of a pulse from within the therapy regimen relative to the therapy trigger, and instruct the delivery circuit to route the pulse to selected contacts of the at least two contacts, wherein initiating the therapy regimen includes the controller executing the triggering instruction set.

11. A method as in claim 9, wherein the controller further comprises an executable triggering instruction set adapted to identify a therapy trigger, identify a therapy window for delivery of a pulse from within the therapy regimen relative to the therapy trigger, and instruct the delivery circuit to route the pulse to selected contacts of the at least two contacts, wherein initiating the therapy regimen includes the controller executing the triggering instruction set.

12. A method as in claim 9, wherein the electrosurgical generator includes a trigger circuit adapted to sense a representation of a cardiac signal of a patient, identify a therapy window for delivery of a pulse from within the therapy regimen, and instruct the delivery circuit to route a pulse to selected contacts of the one or more ports, wherein initiating the therapy regimen includes activating the trigger circuit.

13. A method as in claim 9, wherein the electrosurgical generator includes a trigger circuit adapted to receive a representation of a cardiac signal of a patient, identify a therapy window for delivery of a pulse from within the therapy regimen, and instruct the delivery circuit to route the pulse to selected contacts of the one or more ports, wherein initiating the therapy regimen includes activating the trigger circuit.

* * * * *